(12) United States Patent
Ritland

(10) Patent No.: US 7,985,245 B2
(45) Date of Patent: *Jul. 26, 2011

(54) CONNECTION ROD FOR SCREW OR HOOK POLYAXIAL SYSTEM AND METHOD OF USE

(76) Inventor: Stephen Ritland, Flagstaff, AZ (US)

(*) Notice: Subject to any disclaimer, the term of this patent is extended or adjusted under 35 U.S.C. 154(b) by 994 days.

This patent is subject to a terminal disclaimer.

(21) Appl. No.: 11/283,006

(22) Filed: Nov. 18, 2005

(65) Prior Publication Data

US 2006/0079899 A1 Apr. 13, 2006

Related U.S. Application Data

(62) Division of application No. 10/262,574, filed on Sep. 30, 2002, now Pat. No. 7,207,992.

(60) Provisional application No. 60/325,809, filed on Sep. 28, 2001.

(51) Int. Cl.
A61B 17/70 (2006.01)

(52) U.S. Cl. .................. 606/266; 606/271; 606/279

(58) Field of Classification Search .................. 606/246, 606/256–274, 275–279, 86 A; 403/56, 76, 403/90, 114–115, 122–144
See application file for complete search history.

(56) References Cited

U.S. PATENT DOCUMENTS

| 2,191 A | 7/1841 | Pitney |
|---|---|---|
| 569,839 A | 10/1896 | Roeloffs |
| 605,652 A | 6/1898 | Pitt |
| 1,090,746 A | 3/1914 | Nourse |
| 1,097,978 A | 5/1914 | Johnson |
| 3,467,079 A | 9/1969 | James |
| 3,470,872 A | 10/1969 | Grieshaber |
| 3,875,595 A | 4/1975 | Froning |
| 3,893,454 A | 7/1975 | Hagelin |
| 4,041,939 A | 8/1977 | Hall |
| 4,232,660 A | 11/1980 | Coles |
| 4,440,168 A | 4/1984 | Warren |

(Continued)

FOREIGN PATENT DOCUMENTS

CA 2320821 8/1999

(Continued)

OTHER PUBLICATIONS

Office Action dated Aug. 21, 2008, received in related Australian Application No. 2006200772.

(Continued)

*Primary Examiner* — Eduardo C Robert
*Assistant Examiner* — Steven J Cotroneo
(74) *Attorney, Agent, or Firm* — Holme Roberts & Owen LLP

(57) ABSTRACT

A low-profile surgical implant assembly is provided that includes a connector device that is an integral part of a rod, the connector device allowing the rod to be attached directly to a bone screw, such as a pedicle screw. Another aspect of the invention is a clamp device that allows the length of a rod spanning to attachment devices to be adjusted at the time of implantation, and further allows the clamp device to be secured by tightening a securing end of the clamp at the attachment device. The assemblies are useful for insertion into bone and connecting a foreign object to bone via a polyaxial coupling mechanism. A method for implanting the assembly is also provided.

10 Claims, 17 Drawing Sheets

U.S. PATENT DOCUMENTS

| | | |
|---|---|---|
| 4,481,947 A | 11/1984 | Chester |
| 4,545,374 A | 10/1985 | Jacobson |
| 4,573,448 A | 3/1986 | Kambin |
| 4,617,922 A | 10/1986 | Griggs |
| 4,620,460 A | 11/1986 | Gonzales, Jr. |
| 4,686,972 A | 8/1987 | Kurland |
| 4,736,738 A | 4/1988 | Lipovsek |
| 4,743,260 A | 5/1988 | Burton |
| 4,747,394 A | 5/1988 | Watanabe |
| 4,798,111 A | 1/1989 | Cheeseman |
| 4,803,976 A | 2/1989 | Frigg |
| 4,817,587 A | 4/1989 | Janese |
| 4,862,891 A | 9/1989 | Smith |
| 4,863,423 A | 9/1989 | Wallace |
| 4,882,958 A | 11/1989 | McNeely |
| 4,889,112 A | 12/1989 | Schachner et al. |
| 4,946,458 A | 8/1990 | Harms et al. |
| 4,995,875 A | 2/1991 | Coes |
| 5,002,542 A | 3/1991 | Frigg |
| 5,002,576 A | 3/1991 | Fuhrmann et al. |
| 5,018,507 A | 5/1991 | Montaldi |
| 5,024,213 A | 6/1991 | Asher et al. |
| 5,026,373 A | 6/1991 | Ray et al. |
| 5,030,220 A | 7/1991 | Howland |
| 5,030,223 A | 7/1991 | Anderson et al. |
| 5,035,232 A | 7/1991 | Lutze et al. |
| 5,048,379 A | 9/1991 | Gramera |
| 5,052,373 A | 10/1991 | Michelson |
| 5,055,104 A | 10/1991 | Ray |
| 5,084,043 A | 1/1992 | Hertzmann |
| 5,098,435 A | 3/1992 | Stednitz |
| 5,106,376 A | 4/1992 | Mononen |
| 5,129,899 A | 7/1992 | Small et al. |
| 5,129,900 A | 7/1992 | Asher et al. |
| 5,133,720 A | 7/1992 | Greenberg |
| 5,135,525 A | 8/1992 | Biscoping |
| 5,148,724 A | 9/1992 | Rexford |
| 5,158,543 A | 10/1992 | Lazarus |
| 5,165,306 A | 11/1992 | Hellon |
| 5,195,541 A | 3/1993 | Obenchain |
| 5,217,007 A | 6/1993 | Ciaglia |
| 5,275,600 A | 1/1994 | Allard et al. |
| 5,275,611 A | 1/1994 | Behl |
| 5,279,567 A | 1/1994 | Ciaglia |
| 5,292,309 A | 3/1994 | Van Tassel |
| 5,303,694 A | 4/1994 | Mikhail |
| 5,304,179 A | 4/1994 | Wagner |
| 5,306,275 A | 4/1994 | Bryan |
| 5,306,309 A | 4/1994 | Wagner et al. |
| 5,312,360 A | 5/1994 | Behl |
| 5,312,405 A | 5/1994 | Korotko et al. |
| 5,330,473 A | 7/1994 | Howland |
| 5,330,474 A | 7/1994 | Lin |
| 5,330,476 A | 7/1994 | Hiot et al. |
| 5,356,413 A | 10/1994 | Martins et al. |
| 5,363,841 A | 11/1994 | Coker |
| 5,415,661 A | 5/1995 | Holmes |
| 5,423,816 A | 6/1995 | Lin |
| 5,431,639 A | 7/1995 | Shaw |
| 5,431,651 A | 7/1995 | Goble |
| D361,381 S | 8/1995 | Koros et al. |
| 5,439,464 A | 8/1995 | Shapiro |
| 5,466,238 A | 11/1995 | Lin |
| 5,472,426 A | 12/1995 | Bonati |
| 5,474,555 A | 12/1995 | Puno et al. |
| 5,480,401 A | 1/1996 | Navas |
| 5,484,440 A | 1/1996 | Allard |
| 5,489,274 A | 2/1996 | Chu |
| 5,489,308 A | 2/1996 | Kuslich et al. |
| 5,498,262 A | 3/1996 | Bryan |
| 5,499,983 A | 3/1996 | Hughes |
| 5,501,684 A | 3/1996 | Schlapfer et al. |
| 5,512,038 A | 4/1996 | O'Neal et al. |
| 5,545,166 A | 8/1996 | Howland |
| 5,549,612 A | 8/1996 | Yapp et al. |
| 5,558,622 A | 9/1996 | Greenberg |
| 5,562,663 A | 10/1996 | Wisenewski et al. |
| 5,565,502 A | 10/1996 | Glimcher et al. |
| 5,569,300 A | 10/1996 | Redmon |
| 5,584,831 A | 12/1996 | McKay |
| 5,584,833 A | 12/1996 | Fournet-Fayard et al. |
| 5,591,166 A * | 1/1997 | Bernhardt et al. ............ 606/266 |
| 5,591,235 A | 1/1997 | Kuslich |
| 5,593,409 A | 1/1997 | Michelson |
| 5,601,550 A | 2/1997 | Esser |
| 5,603,714 A | 2/1997 | Kaneda et al. |
| 5,611,778 A | 3/1997 | Brinon |
| 5,613,968 A | 3/1997 | Lin |
| 5,628,740 A | 5/1997 | Mullane |
| 5,643,263 A | 7/1997 | Simonson |
| 5,643,264 A | 7/1997 | Sherman et al. |
| 5,645,544 A | 7/1997 | Tai et al. |
| 5,645,599 A | 7/1997 | Samani |
| 5,667,506 A | 9/1997 | Sutterlin |
| 5,683,392 A | 11/1997 | Richelsoph et al. |
| 5,683,463 A | 11/1997 | Godefroy et al. |
| 5,687,739 A | 11/1997 | McPherson |
| 5,690,632 A | 11/1997 | Schwartz et al. |
| 5,691,397 A | 11/1997 | Glimcher et al. |
| 5,695,993 A | 12/1997 | Fukudome et al. |
| 5,702,455 A | 12/1997 | Saggar |
| 5,716,355 A | 2/1998 | Jackson et al. |
| 5,716,415 A | 2/1998 | Steffee |
| 5,725,528 A | 3/1998 | Errico et al. |
| 5,735,850 A | 4/1998 | Baumgartner et al. |
| 5,735,851 A * | 4/1998 | Errico et al. ................ 606/266 |
| 5,735,899 A | 4/1998 | Schwartz et al. |
| 5,743,853 A | 4/1998 | Lauderdale |
| 5,746,720 A | 5/1998 | Stouder, Jr. |
| 5,746,741 A | 5/1998 | Kraus et al. |
| 5,752,957 A | 5/1998 | Ralph et al. |
| 5,766,221 A | 6/1998 | Benderev et al. |
| 5,766,253 A | 6/1998 | Brosnahan, III |
| 5,772,582 A | 6/1998 | Huttner et al. |
| 5,782,832 A | 7/1998 | Larsen et al. |
| 5,785,648 A | 7/1998 | Min |
| 5,785,710 A | 7/1998 | Michelson |
| 5,785,712 A | 7/1998 | Runciman et al. |
| 5,792,044 A | 8/1998 | Foley |
| 5,797,912 A | 8/1998 | Runciman et al. |
| 5,800,435 A * | 9/1998 | Errico et al. ................ 606/261 |
| 5,810,816 A | 9/1998 | Roussouly et al. |
| 5,810,817 A | 9/1998 | Roussouly et al. |
| D399,955 S | 10/1998 | Koros et al. |
| 5,816,257 A | 10/1998 | Chin |
| 5,827,328 A | 10/1998 | Buttermann |
| 5,836,948 A | 11/1998 | Zucherman et al. |
| RE36,020 E | 12/1998 | Moore et al. |
| 5,851,207 A | 12/1998 | Cesarone |
| 5,860,977 A | 1/1999 | Zucherman et al. |
| 5,865,847 A | 2/1999 | Kohrs et al. |
| 5,865,848 A | 2/1999 | Baker |
| 5,876,404 A | 3/1999 | Zucherman et al. |
| 5,882,344 A | 3/1999 | Stouder, Jr. |
| 5,885,285 A | 3/1999 | Simonson |
| 5,885,299 A | 3/1999 | Winslow et al. |
| 5,885,300 A | 3/1999 | Tokuhashi et al. |
| 5,891,147 A | 4/1999 | Moskovitz et al. |
| 5,895,352 A | 4/1999 | Kleiner |
| 5,895,390 A | 4/1999 | Moran et al. |
| 5,897,593 A | 4/1999 | Kohrs et al. |
| 5,899,901 A | 5/1999 | Middleton |
| 5,902,231 A | 5/1999 | Foley |
| 5,902,304 A | 5/1999 | Walker et al. |
| 5,904,650 A | 5/1999 | Wells |
| 5,906,616 A | 5/1999 | Pavlov et al. |
| 5,913,818 A | 6/1999 | Co et al. |
| 5,928,139 A | 7/1999 | Koros |
| 5,928,233 A | 7/1999 | Apfelbaum et al. |
| 5,931,838 A | 8/1999 | Vito |
| 5,938,663 A | 8/1999 | Petreto |
| 5,944,658 A | 8/1999 | Koros et al. |
| 5,947,965 A | 9/1999 | Bryan |
| 5,954,635 A | 9/1999 | Foley |
| 5,954,671 A | 9/1999 | O'Neil |
| 5,961,516 A | 10/1999 | Graf |
| 5,967,970 A | 10/1999 | Cowan |

| | | | | | | |
|---|---|---|---|---|---|---|
| 5,968,098 A | 10/1999 | Winslow | | 6,267,765 B1 | 7/2001 | Taylor et al. |
| 5,971,920 A | 10/1999 | Nagel | | 6,270,498 B1 | 8/2001 | Michelson |
| 5,976,135 A | 11/1999 | Sherman et al. | | 6,273,914 B1 | 8/2001 | Papas |
| 5,976,146 A | 11/1999 | Ogawa | | 6,283,966 B1 | 9/2001 | Houfburg |
| 5,984,924 A | 11/1999 | Asher et al. | | 6,287,309 B1 | 9/2001 | Baccelli et al. |
| 5,996,447 A | 12/1999 | Bayouth | | 6,287,313 B1 | 9/2001 | Sasso |
| 5,997,539 A | 12/1999 | Errico et al. | | 6,287,343 B1 | 9/2001 | Kuslich et al. |
| 6,004,322 A | 12/1999 | Bernstein | | 6,290,700 B1 | 9/2001 | Schmotzer |
| 6,007,487 A | 12/1999 | Foley et al. | | 6,293,949 B1 | 9/2001 | Justis et al. |
| 6,010,520 A | 1/2000 | Pattison | | 6,296,609 B1 | 10/2001 | Brau |
| 6,017,342 A | 1/2000 | Rinner | | 6,299,614 B1 | 10/2001 | Kretschmer et al. |
| 6,027,533 A | 2/2000 | Olerud | | 6,302,842 B1 | 10/2001 | Auerbach et al. |
| 6,045,579 A | 4/2000 | Hochshuler et al. | | 6,309,390 B1 | 10/2001 | Le Couedic et al. |
| 6,048,342 A | 4/2000 | Zucherman et al. | | 6,309,391 B1 | 10/2001 | Crandall et al. |
| 6,050,997 A * | 4/2000 | Mullane .................. 606/250 | | 6,312,432 B1 | 11/2001 | Leppelmeier |
| 6,063,088 A | 5/2000 | Winslow | | 6,332,883 B1 | 12/2001 | Zucherman et al. |
| 6,068,630 A | 5/2000 | Zucherman et al. | | 6,342,057 B1 | 1/2002 | Brace |
| 6,074,390 A | 6/2000 | Zucherman et al. | | 6,348,058 B1 | 2/2002 | Melkent et al. |
| 6,074,393 A | 6/2000 | Sitoto | | 6,354,176 B1 | 3/2002 | Nordlin |
| 6,080,155 A | 6/2000 | Michelson | | 6,355,038 B1 | 3/2002 | Pisharodi |
| 6,080,193 A | 6/2000 | Hochshuler et al. | | 6,361,541 B1 | 3/2002 | Barnhart |
| 6,081,741 A | 6/2000 | Hollis | | 6,368,320 B1 | 4/2002 | Le Couedic et al. |
| 6,083,225 A | 7/2000 | Winslow et al. | | 6,368,350 B1 | 4/2002 | Erickson et al. |
| 6,083,226 A | 7/2000 | Fiz | | 6,368,351 B1 | 4/2002 | Glenn et al. |
| 6,090,112 A | 7/2000 | Zucherman et al. | | 6,371,959 B1 | 4/2002 | Trice |
| 6,102,948 A | 8/2000 | Brosnahan, III | | 6,371,968 B1 | 4/2002 | Kogasaka |
| 6,113,602 A | 9/2000 | Sand | | 6,391,058 B1 | 5/2002 | Kuslich et al. |
| 6,117,137 A | 9/2000 | Halm et al. | | 6,395,033 B1 | 5/2002 | Pepper |
| 6,117,174 A | 9/2000 | Nolan | | 6,418,821 B1 | 7/2002 | Yamakawa |
| 6,120,434 A | 9/2000 | Kimura | | 6,425,901 B1 | 7/2002 | Zhu et al. |
| 6,120,506 A | 9/2000 | Kohrs et al. | | 6,428,472 B1 | 8/2002 | Haas |
| 6,123,705 A | 9/2000 | Michelson | | 6,440,169 B1 | 8/2002 | Elberg et al. |
| 6,123,706 A | 9/2000 | Lange | | 6,440,170 B1 | 8/2002 | Jackson |
| 6,132,430 A | 10/2000 | Wagner | | 6,443,953 B1 | 9/2002 | Perra et al. |
| D433,296 S | 11/2000 | Yamakawa | | 6,443,989 B1 | 9/2002 | Jackson |
| 6,146,383 A | 11/2000 | Studer et al. | | 6,461,330 B1 | 10/2002 | Miyagi |
| 6,149,652 A | 11/2000 | Zucherman et al. | | 6,461,359 B1 | 10/2002 | Tribus et al. |
| 6,149,686 A | 11/2000 | Kuslich et al. | | 6,471,724 B2 | 10/2002 | Zdeblick |
| 6,152,871 A | 11/2000 | Foley | | 6,478,798 B1 | 11/2002 | Howland |
| 6,152,926 A | 11/2000 | Zucherman et al. | | D466,766 S | 12/2002 | Marty |
| 6,156,006 A | 12/2000 | Brosens | | 6,506,151 B2 | 1/2003 | Estes |
| 6,156,038 A | 12/2000 | Zucherman et al. | | 6,520,907 B1 | 2/2003 | Foley |
| 6,159,179 A | 12/2000 | Simonson | | 6,524,238 B2 | 2/2003 | Velikaris et al. |
| 6,162,170 A | 12/2000 | Foley | | 6,530,880 B2 | 3/2003 | Pagliuca |
| 6,162,236 A | 12/2000 | Osada | | 6,530,926 B1 | 3/2003 | Davison |
| D436,513 S | 1/2001 | Yamakawa | | 6,540,756 B1 | 4/2003 | Vaughan |
| 6,176,823 B1 | 1/2001 | Foley | | 6,551,320 B2 | 4/2003 | Lieberman |
| 6,176,861 B1 | 1/2001 | Bernstein et al. | | 6,554,831 B1 | 4/2003 | Rivard et al. |
| 6,179,838 B1 | 1/2001 | Fiz | | 6,562,046 B2 | 5/2003 | Sasso |
| D438,074 S | 2/2001 | Marr | | 6,562,073 B2 | 5/2003 | Foley |
| 6,183,471 B1 | 2/2001 | Zucherman et al. | | 6,565,569 B1 | 5/2003 | Assaker et al. |
| 6,187,005 B1 | 2/2001 | Brace et al. | | 6,569,164 B1 | 5/2003 | Assaker et al. |
| 6,190,387 B1 | 2/2001 | Zucherman et al. | | 6,576,017 B2 | 6/2003 | Foley |
| 6,190,414 B1 | 2/2001 | Young et al. | | 6,579,292 B2 | 6/2003 | Taylor |
| 6,196,696 B1 | 3/2001 | Shiao | | 6,585,738 B1 | 7/2003 | Mangione et al. |
| 6,196,969 B1 | 3/2001 | Bester et al. | | 6,585,769 B1 | 7/2003 | Muhanna et al. |
| 6,197,002 B1 | 3/2001 | Peterson | | 6,595,993 B2 | 7/2003 | Donno et al. |
| 6,206,822 B1 | 3/2001 | Foley | | 6,610,062 B2 * | 8/2003 | Bailey et al. .................. 606/261 |
| 6,206,826 B1 | 3/2001 | Mathews et al. | | 6,626,904 B1 * | 9/2003 | Jammet et al. ................ 606/266 |
| 6,206,885 B1 | 3/2001 | Ghahremani et al. | | 6,626,906 B1 | 9/2003 | Young |
| 6,206,922 B1 | 3/2001 | Zdeblick et al. | | 6,648,887 B2 | 11/2003 | Ashman |
| 6,206,923 B1 | 3/2001 | Boyd et al. | | 6,671,725 B1 | 12/2003 | Noel, Jr. et al. |
| 6,210,413 B1 | 4/2001 | Justis et al. | | 6,676,661 B1 | 1/2004 | Martin Benlloch et al. |
| 6,214,004 B1 | 4/2001 | Coker | | 6,679,833 B2 | 1/2004 | Smith |
| 6,217,509 B1 | 4/2001 | Foley | | 6,682,532 B2 | 1/2004 | Johnson et al. |
| 6,224,597 B1 | 5/2001 | Coker | | 6,685,705 B1 | 2/2004 | Taylor |
| 6,224,608 B1 | 5/2001 | Ciccolella | | 6,692,434 B2 | 2/2004 | Ritland |
| 6,224,631 B1 | 5/2001 | Kohrs et al. | | 6,736,816 B2 | 5/2004 | Ritland |
| 6,231,575 B1 | 5/2001 | Krag | | 6,743,257 B2 | 6/2004 | Castro |
| 6,235,030 B1 | 5/2001 | Zucherman et al. | | 6,749,613 B1 | 6/2004 | Conchy et al. |
| 6,238,397 B1 | 5/2001 | Zucherman et al. | | 6,749,614 B2 | 6/2004 | Teitelbaum |
| 6,245,072 B1 | 6/2001 | Zdeblick et al. | | 6,752,832 B2 | 6/2004 | Neumann |
| 6,248,104 B1 | 6/2001 | Chopin et al. | | 6,761,719 B2 | 7/2004 | Justis et al. |
| 6,248,106 B1 | 6/2001 | Ferree | | 6,783,528 B2 | 8/2004 | Vincent-Prestigiacomo |
| 6,258,097 B1 | 7/2001 | Cook | | 6,851,430 B2 | 2/2005 | Tsou |
| 6,261,287 B1 | 7/2001 | Metz-Stavenhagen | | 6,875,211 B2 | 4/2005 | Nichols et al. |
| 6,264,658 B1 | 7/2001 | Lee et al. | | 6,916,319 B2 | 7/2005 | Munting |
| 6,267,763 B1 | 7/2001 | Castro | | 6,916,330 B2 | 7/2005 | Simonson |
| 6,267,764 B1 | 7/2001 | Elberg | | 6,929,606 B2 | 8/2005 | Ritland |

| | | |
|---|---|---|
| 6,951,538 B2 | 10/2005 | Ritland |
| 6,955,678 B2 | 10/2005 | Gabriel et al. |
| 6,966,910 B2 | 11/2005 | Ritland |
| 6,974,480 B2 | 12/2005 | Messerli et al. |
| 6,991,632 B2 | 1/2006 | Ritland |
| 7,008,431 B2 | 3/2006 | Simonson |
| 7,166,073 B2 | 1/2007 | Ritland |
| 7,207,992 B2 | 4/2007 | Ritland |
| 2001/0005796 A1 | 6/2001 | Zdeblick et al. |
| 2001/0010021 A1 | 7/2001 | Boyd et al. |
| 2001/0012942 A1 | 8/2001 | Estes |
| 2001/0027320 A1 | 10/2001 | Sasso |
| 2001/0047207 A1 | 11/2001 | Michelson |
| 2002/0011135 A1 | 1/2002 | Hall |
| 2002/0016592 A1 | 2/2002 | Branch |
| 2002/0022764 A1 | 2/2002 | Smith |
| 2002/0029082 A1 | 3/2002 | Muhanna |
| 2002/0049368 A1 | 4/2002 | Ritland |
| 2002/0052603 A1 | 5/2002 | Nichols |
| 2002/0058948 A1 | 5/2002 | Arlettaz |
| 2002/0068973 A1 | 6/2002 | Jackson |
| 2002/0068975 A1 | 6/2002 | Teitelbaum et al. |
| 2002/0077632 A1 | 6/2002 | Tsou |
| 2002/0082695 A1 | 6/2002 | Neumann |
| 2002/0107571 A1 | 8/2002 | Foley |
| 2002/0107572 A1 | 8/2002 | Foley et al. |
| 2002/0111625 A1 | 8/2002 | Richelsoph et al. |
| 2002/0120270 A1 | 8/2002 | Trieu et al. |
| 2002/0123668 A1 | 9/2002 | Ritland |
| 2002/0143235 A1 | 10/2002 | Pagliuca |
| 2003/0045874 A1 | 3/2003 | Thomas |
| 2003/0083689 A1 | 5/2003 | Simonson |
| 2003/0093078 A1 | 5/2003 | Ritland |
| 2003/0109880 A1 | 6/2003 | Shirado et al. |
| 2003/0139812 A1 | 7/2003 | Garcia et al. |
| 2003/0144665 A1 | 7/2003 | Munting |
| 2003/0171749 A1 | 9/2003 | LeCouedic et al. |
| 2003/0171751 A1 | 9/2003 | Ritland |
| 2003/0187431 A1 | 10/2003 | Simonson |
| 2003/0191470 A1 | 10/2003 | Ritland |
| 2003/0220689 A1 | 11/2003 | Ritland |
| 2003/0236447 A1 | 12/2003 | Ritland |
| 2004/0002708 A1 | 1/2004 | Ritland |
| 2004/0106997 A1 | 6/2004 | Lieberson |
| 2004/0138534 A1 | 7/2004 | Ritland |
| 2004/0172023 A1 | 9/2004 | Ritland |
| 2004/0181223 A1 | 9/2004 | Ritland |
| 2004/0254428 A1 | 12/2004 | Ritland |
| 2005/0004593 A1 | 1/2005 | Simonson |
| 2005/0020920 A1 | 1/2005 | Ritland |
| 2005/0027360 A1 | 2/2005 | Webb et al. |
| 2005/0119656 A1 | 6/2005 | Ferrante et al. |
| 2005/0143737 A1 | 6/2005 | Pafford et al. |
| 2005/0149023 A1 | 7/2005 | Ritland |
| 2005/0149191 A1 | 7/2005 | Cragg et al. |
| 2005/0203517 A1 | 9/2005 | Jahng et al. |
| 2005/0203519 A1 | 9/2005 | Harms et al. |
| 2005/0209694 A1 | 9/2005 | Loeb |
| 2005/0228233 A1 | 10/2005 | Ritland |
| 2006/0009768 A1 | 1/2006 | Ritland |
| 2006/0041259 A1 | 2/2006 | Paul et al. |
| 2006/0064090 A1 | 3/2006 | Park |
| 2006/0069390 A1 | 3/2006 | Frigg et al. |
| 2006/0079899 A1 | 4/2006 | Ritland |
| 2006/0195087 A1 | 8/2006 | Sacher et al. |
| 2007/0016193 A1 | 1/2007 | Ritland |

FOREIGN PATENT DOCUMENTS

| | | |
|---|---|---|
| DE | 9004960 | 10/1991 |
| EP | 0820731 | 1/1998 |
| FR | 2796828 | 2/2001 |
| FR | 2812185 | 2/2002 |
| JP | 6-3551 | 2/1994 |
| JP | 2000-33091 | 2/2000 |
| WO | 96/29947 | 10/1996 |
| WO | 97-06742 | 2/1997 |
| WO | WO 99/40866 | 8/1999 |
| WO | 0018306 | 4/2000 |
| WO | 00/57801 | 10/2000 |
| WO | 01/67973 | 9/2001 |
| WO | 0202022 | 1/2002 |
| WO | 0207621 | 1/2002 |
| WO | 02/36026 | 2/2002 |
| WO | 02060330 | 8/2002 |
| WO | 03026523 | 4/2003 |
| WO | 03073908 | 9/2003 |
| WO | 03094699 | 11/2003 |
| WO | 2004075778 | 9/2004 |
| WO | 2004089244 | 10/2004 |

OTHER PUBLICATIONS

Caspar; "Technique of Microsurgery: Microsurgery of the Lumbar Spine: Principles and Techniques in Spine Surgery"; Aspen Publications; 1990; 105-122.

Hilton et al.; "Meditronic Sofamor Danek METRX Microdiscectomy Surgical Technique Brochure"; 2000.

Kambin; "Arthroscopic Microdiscectomy: Minimal Intervention in Spinal Surgery"; National Library of Medicine; 1991; 67-100.

Kambin; "Percutaneous Posterolateral Discectomy"; Clincial Orthopaedics and Related Research, Section II; 145-154119.

Savitz; "Same-Day Microsurgical Arthroscopic Latera-Approach Laser-Assisted (SMALL) Fluoroscopic Discectomy"; Journal of Neurosurgery; Jun. 1994; 1039-1045.

Schaffer et al.; "Percutaneous Posterolateral Lumbar Discectomy and Decompression with a 6.9 Millimeter Cannula"; Journal of Bone and Joint Surgery; 1991; 822-831.

Sofamor Danek Video Systems Brochure.

Wiltse; "New Uses and Refinements of the Paraspinal Approach to the Lumbar Spine"; Spine; 1988; 13(6):696-706.

Office Action mailed Nov. 21, 2008, in related, co-pending Australian Application No. 2004216131.

International Search Report for PCT Application Serial No. PCT/US02/31201 mailed Feb. 19, 2003.

Written Opinion for PCT Application Serial No. PCT/US02/31201 mailed Aug. 14, 2003.

International Preliminary Examination Report for PCT Application Serial No. PCT/US02/31201 mailed Jan. 20, 2004.

International Search Report for PCT Application Serial No. PCT/US2004/005751 mailed Mar. 3, 2005.

Written Opinion for PCT Application Serial No. PCT/US2004/005751 mailed Mar. 3, 2005.

International Preliminary Report on Patentability for PCT Application Serial No. PCT/US2004/005751 mailed Sep. 9, 2005.

U.S. Appl. No. 10/165,991, Simonson.

U.S. Appl. No. 11/425,987, Ritland.

China Chemical Reporter, "Rapid Development of Polyether Ether Ketone", CNCIC Chemdata Inc., 2004, 2 pages.

Green, "Body Building—Medical Materials for Systems and Scaffolding," Materials World, Journal of the Institute of Materials, vol. 10, No. 2, 2001, 4 pages.

Green, "Effects of Gamma Sterilisation on Implant Grade Polyetheretherketone," Invibio Inc., Lancashire, United Kingdom, undated, 1 page.

Green, "In Vivo Biostability Study on Polyaryletheretherketone Biomaterial," Invibio Inc., Lancashire, United Kingdom, undated, 2 pages.

Green, et al., "A Polyaryletherketone Biomaterial for Use in Medical Implant Applications," Lancashire, United Kingdom, 2001, 1 page.

Green, et al., "Polyetheretherketone Polymer and Compounds for Surgical Applications," Lancashire, United Kingdom, undated, 9 pages.

Green, Stuart, "PEEK-Optima Polymer in the Implantable Medical Device Industry," Invibio Inc., Lancashire, United Kingdom, undated, 2 pages.

Invibio, Biomaterials Solutions, "High Performance PEEK-Optima Biocompatible Polymer Chosen for Dental Abutment Healing Caps," Invibio Inc., Lancashire, United Kingdom, undated, 1 page.

Invibio, Biomaterials Solutions, "High Performance PEEK-Optima Biocompatible Polymer Chosen for New Generation Heart Valve," Invibio Inc., Lancashire, United Kingdom, undated, 1 page.

Invibio, Biomaterials Solutions, "PEEK-Classix," Invibio Inc., Lancashire, United Kingdom, 2003, 2 pages.

Invibio, Biomaterials Solutions, "PEEK-Optima Polymer: Performance Purity Flexibility Endurance," Invibio Inc., Lancashire, United Kingdom, 2004, 3 pages.

Invibio, Biomaterials Solutions, "PEEK-Optima, Composite Hip," Invibio Inc., Lancashire, United Kingdom, undated, 2 pages.

Invibio, Biomaterials Solutions, "PEEK-Optima, Spiked Washers," Invibio Inc., Lancashire, United Kingdom, undated, 1 page.

Tangram Technology Ltd., "Polymer Data File: Polyether Ether Keotone-PEEK," Available at http://www.tangram.co.uk/TI-Polymer-PEEK.html, 2001, 5 pages.

Web pages, http://www.brainlab.com, Apr. 2, 2002; 5 pp.

"New Minimally Invasive Techniques, Improve Outcome of Spine Surgeries", Medtronic Sofamor Danek.

Office Action dated Dec. 1, 2008, issued in related and co-pending Canadian Application No. 2,415,072.

Office Action dated Sep. 20, 2002, issued in related matter, U.S. Appl. No. 09/898,478.

Amendment and Response filed Jan. 21, 2003, to Office Action, in related matter, U.S. Appl. No. 09/898,478.

Supplemental Amendment and Response filed Mar. 4, 2003, to Office Action, in related matter, U.S. Appl. No. 09/898,478.

Facsimile from Examiner dated Mar. 13, 2003, in related matter, U.S. Appl. No. 09/898,478.

Second Supplemental Amendment and Response filed Mar. 31, 2003, to Office Action, in related matter, U.S. Appl. No. 09/898,478.

Office Action dated Jun. 18, 2003, issued in related matter, U.S. Appl. No. 09/898,478.

Amendment and Response to Election Requirement dated Jul. 17, 2003, in related matter, U.S. Appl. No. 09/898,478.

Final Office Action dated Oct. 7, 2003, issued in related matter, U.S. Appl. No. 09/898,478.

Notice of Allowance dated Nov. 26, 2003, issued in related matter, U.S. Appl. No. 09/898,478.

Amendment after Final Office Action filed Nov. 12, 2003, in related matter, U.S. Appl. No. 09/898,478.

Interview Summary dated Nov. 7, 2003, issued in related matter, U.S. Appl. No. 09/898,478.

Office Action dated Oct. 5, 2006, issued in related matter, U.S. Appl. No. 10/776,094.

Amendment and Response to Office Action filed Feb. 5, 2007, in related matter, U.S. Appl. No. 10/776,094.

Office Action dated Apr. 26, 2007, issued in related matter, U.S. Appl. No. 10/776,094.

Amendment and Response to Office Action filed Jul. 26, 2007, in related matter, U.S. Appl. No. 10/776,094.

Office Action dated Oct. 12, 2007, issued in related matter, U.S. Appl. No. 10/776,094.

Amendment and Response to Office Action filed Feb. 12, 2008, in related matter, U.S. Appl. No. 10/776,094.

Final Office Action dated Apr. 23, 2008, issued in related matter, U.S. Appl. No. 10/776,094.

Amendment and Response to Final Office Action filed Aug. 25, 2008, in related matter, U.S. Appl. No. 10/776,094.

Office Action dated Nov. 14, 2008, issued in related matter, U.S. Appl. No. 10/776,094.

Amendment and Response to Office Action filed Feb. 13, 2009, in related matter, U.S. Appl. No. 10/776,094.

Office Action dated May 22, 2009, issued in related matter, U.S. Appl. No. 10/776,094.

Office Action dated Mar. 28, 2006, issued in related matter, U.S. Appl. No. 10/262,574.

Office Action dated May 27, 2008, issued in related matter, Japanese Application No. 2003-530164.

Notice of Allowance dated Dec. 24, 2008, issued in related matter, Japanese Application No. 2003-530164.

Office Action dated Nov. 21, 2008, issued in related matter, Australian Application No. 2004216131.

Office Action dated May 13, 2008, issued in related matter, U.S. Appl. No. 11/069,390.

Amendment and Response to Office Action filed Sep. 15, 2008, in related matter, U.S. Appl. No. 11/069,390.

Final Office Action dated Dec. 24, 2008, issued in related matter, U.S. Appl. No. 11/069,390.

Amendment and Response to Final Office Action filed Feb. 24, 2009, in related matter, U.S. Appl. No. 11/069,390.

Office Action dated Feb. 23, 2009, issued in related matter, U.S. Appl. No. 11/669,015.

Response to Written Opinion filed Oct. 13, 2001, in related matter, Appl. No. PCT/US2002/031201.

International Search Report dated Sep. 13, 2001, issued in related matter, Application No. PCT/US2001/021205.

International Preliminary Examination Report dated Apr. 23, 2003, issued in related matter, Application No. PCT/US2001/021205.

Written Opinion dated Jun. 10, 2002, issued in related matter, Application No. PCT/US2001/021205.

Notice of Allowance and Approved Claim Set dated Mar. 20, 2009, in related matter, Australian Application No. 2006200772.

Office Action dated May 18, 2009, issued in related matter, U.S. Appl. No. 11/069,390.

European Supplemental Search Report, dated Jul. 29, 2009, issued in European Application No. 02763815.4.

Notice of Allowance dated Dec. 10, 2009, issued in AU Application No. 2004216131.

Office Action dated Feb. 5, 2010, issued in EPO Application No. 01958866.4.

Notice of Allowance dated Nov. 9, 2009, issued in U.S. Appl. No. 11/069,390.

Office Action dated Oct. 21, 2009, issued in JP Application No. 2006-503866.

Supplemental Search Report dated Dec. 23, 2009, issued in EPO Application No. 04714674.1.

Final Office Action dated Nov. 23, 2009, issued in U.S. Appl. No. 11/669,015.

Office Action dated Nov. 4, 2009, issued in CA Application No. 2415072.

Search Report dated Nov. 19, 2009, issued in EPO Application No. 01958866.4.

Notice of Allowance dated Oct. 28, 2009, issued in U.S. Appl. No. 10/776,094.

Office Action dated Feb. 16, 2010, issued in Canadian Application No. 2460183.

Office Action dated Aug. 21, 2008, issued in Australian Application No. 2006200772.

Office Action dated Aug. 31, 2010, issued in European Application No. 01958866.4.

Notice of Allowance dated Aug. 25, 2010, issued in Canadian Application No. 2460183.

Notice of Acceptance dated Aug. 12, 2010, issued in Australian Application No. 2008202467.

Notice of Allowance dated Aug. 30, 2010 w/English translation, issued in JP Application No. 2006-5038866.

EPO Communication regarding Decision to Grant dated Sep. 17, 2010, issued in EPO Application No. 02463815.4.

* cited by examiner

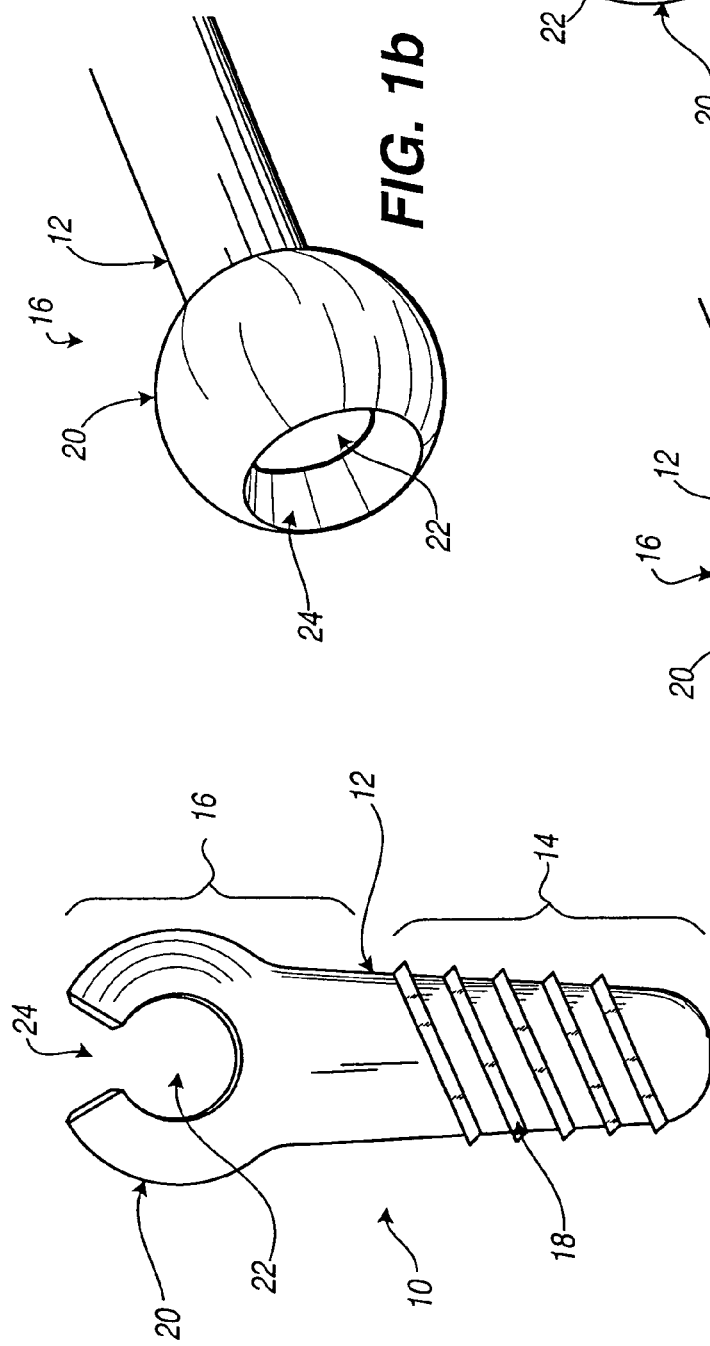
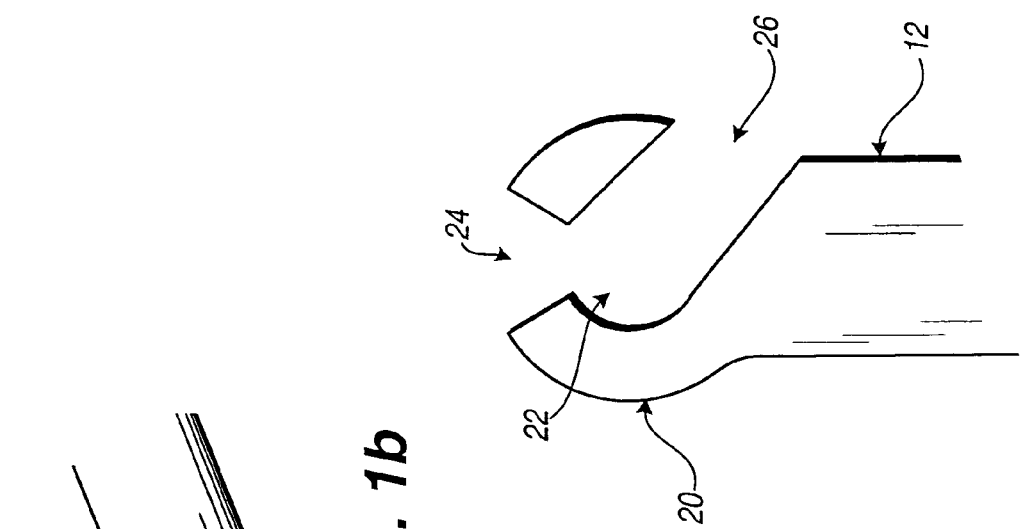
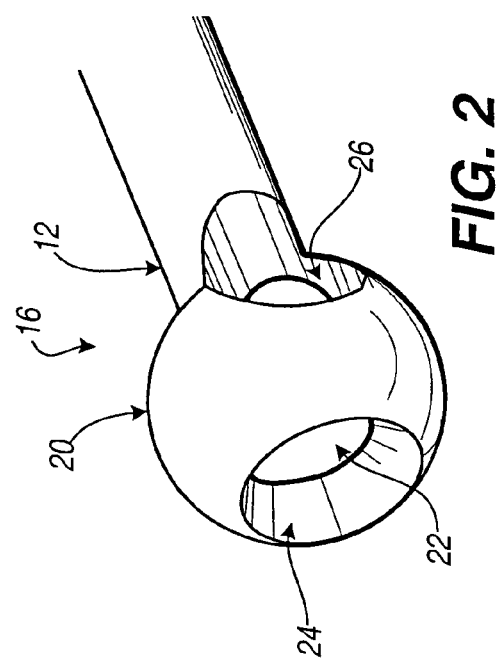
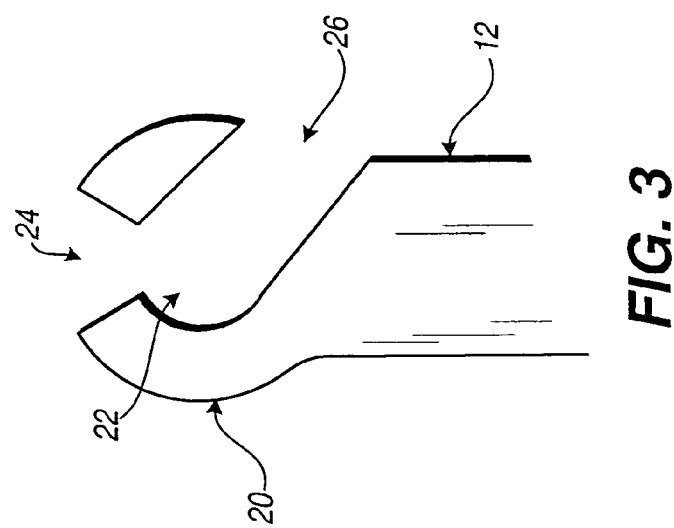
FIG. 1b
FIG. 3
FIG. 2
FIG. 1a

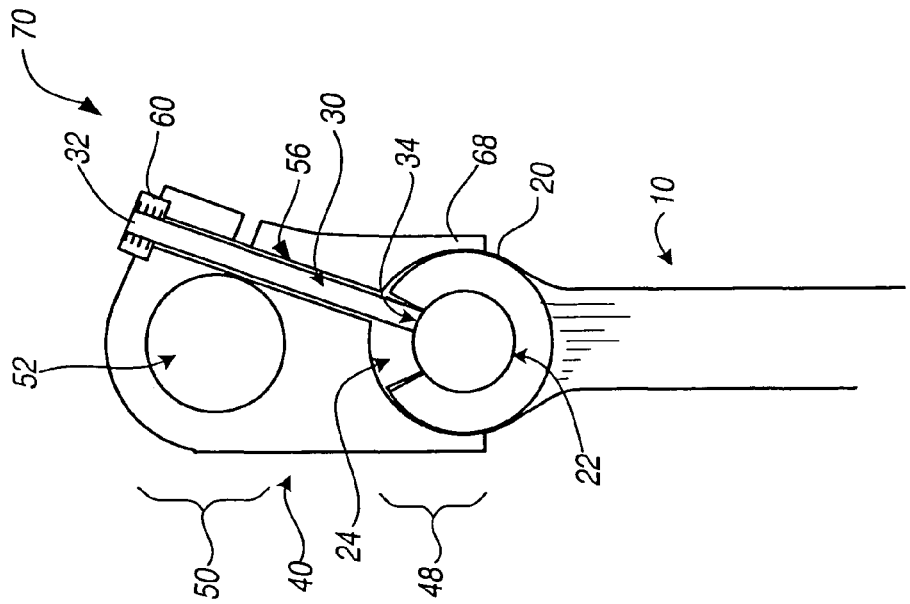
FIG. 17
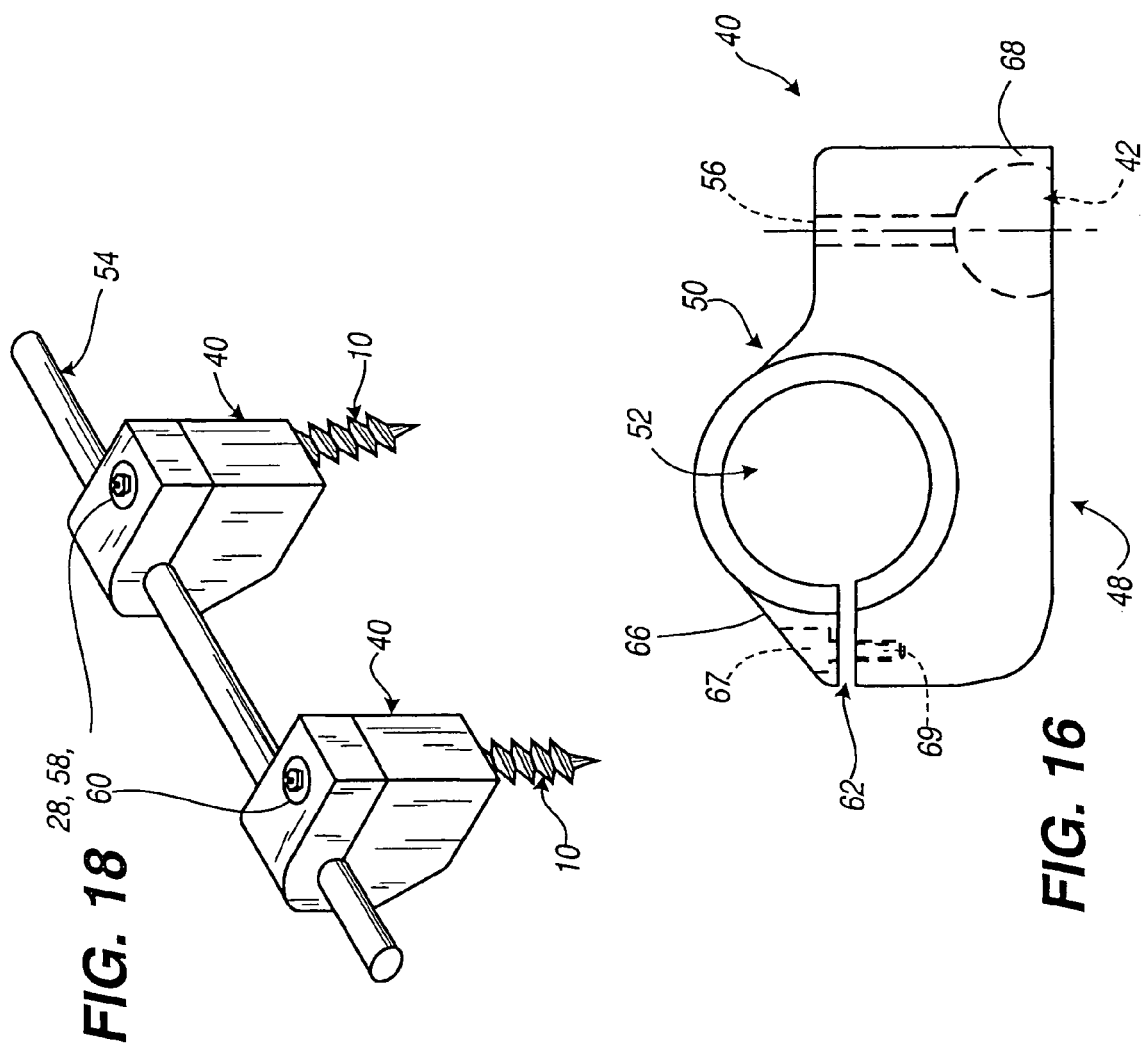
FIG. 18
FIG. 16

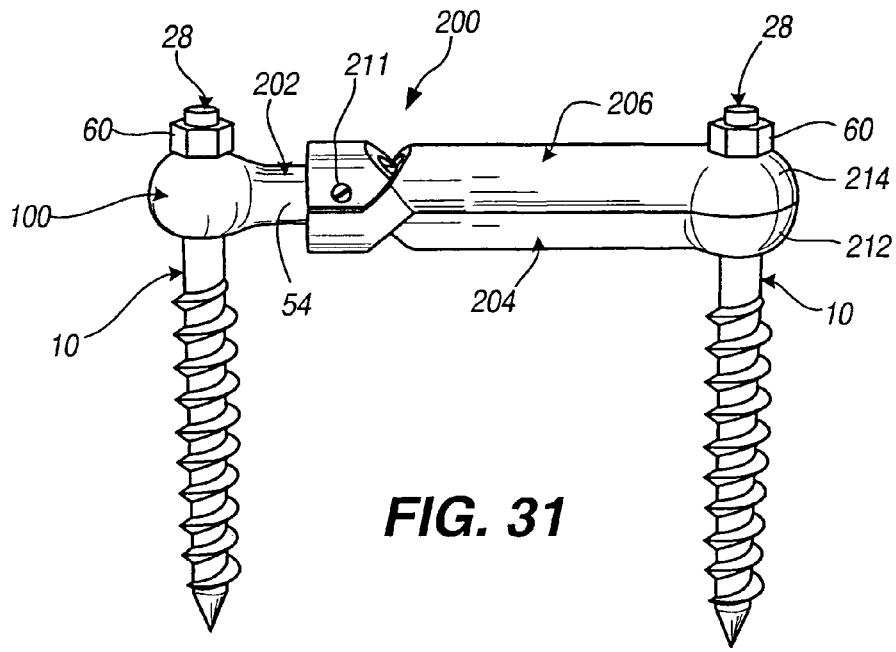
FIG. 31
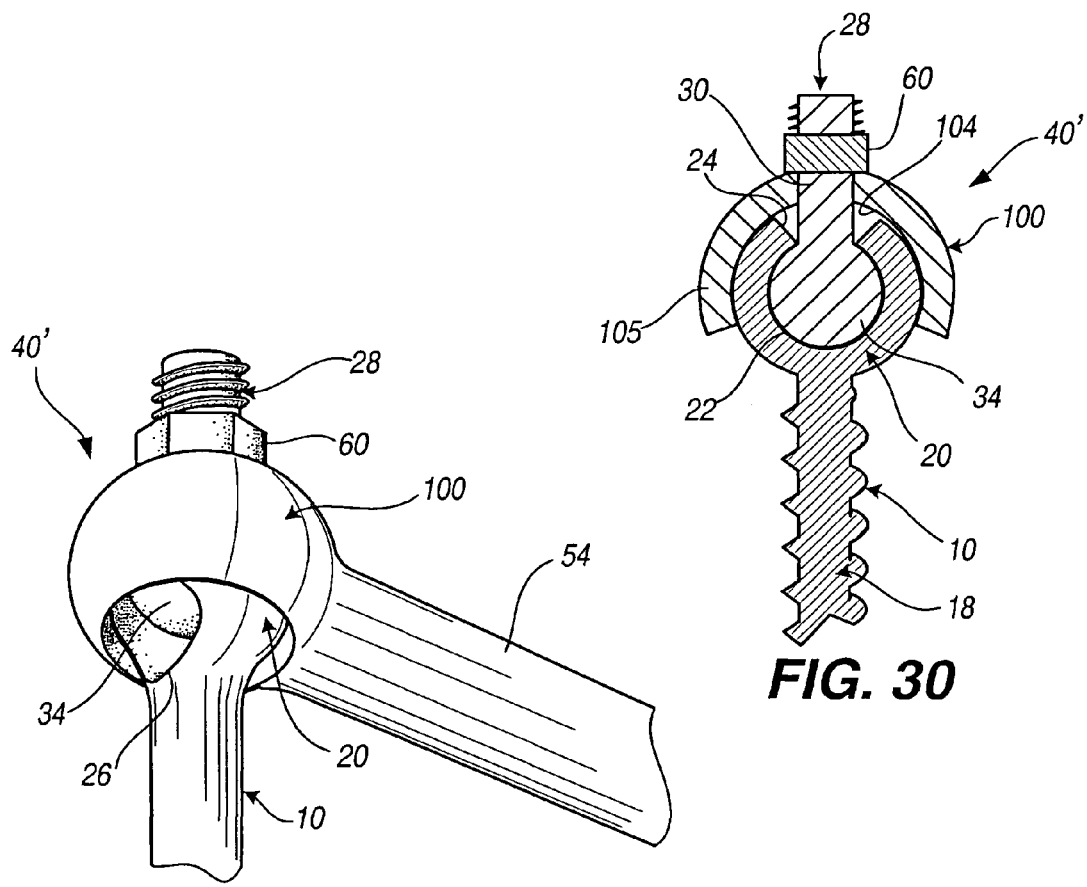
FIG. 30
FIG. 29

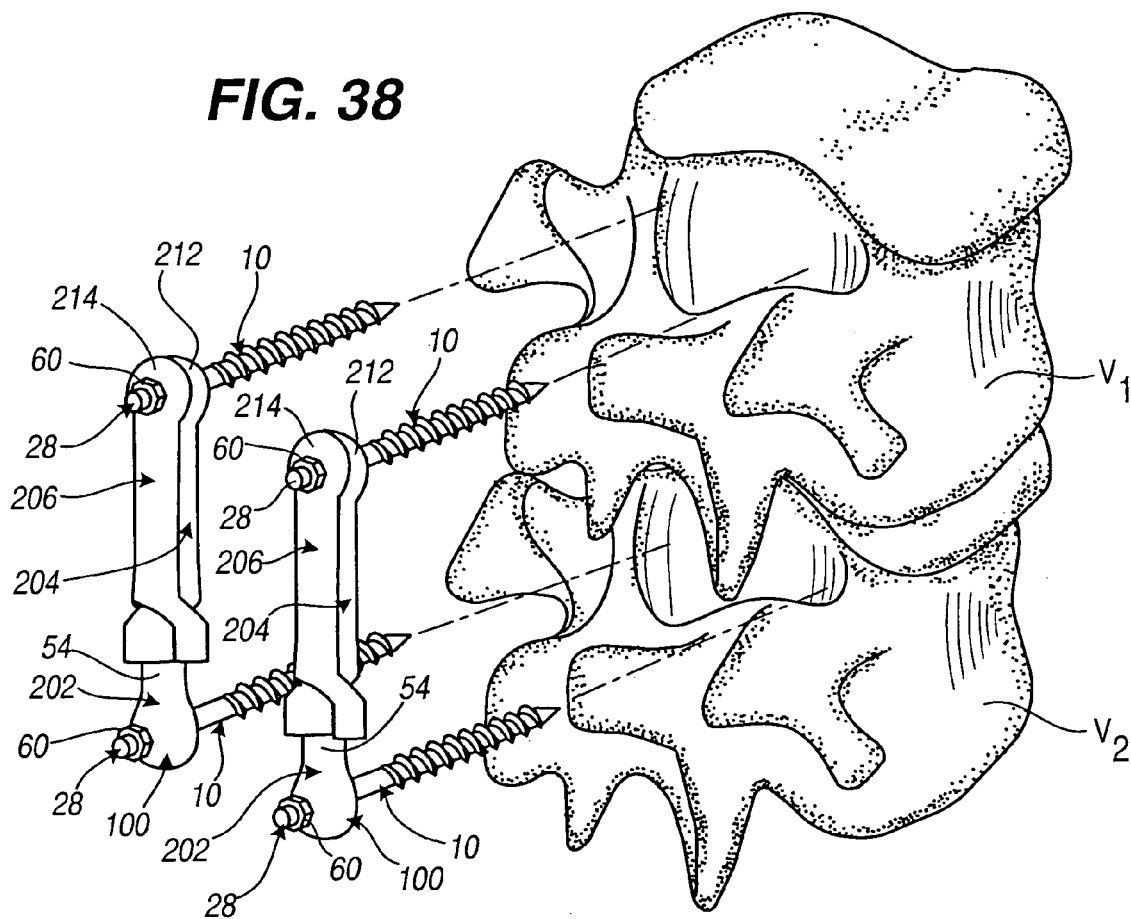

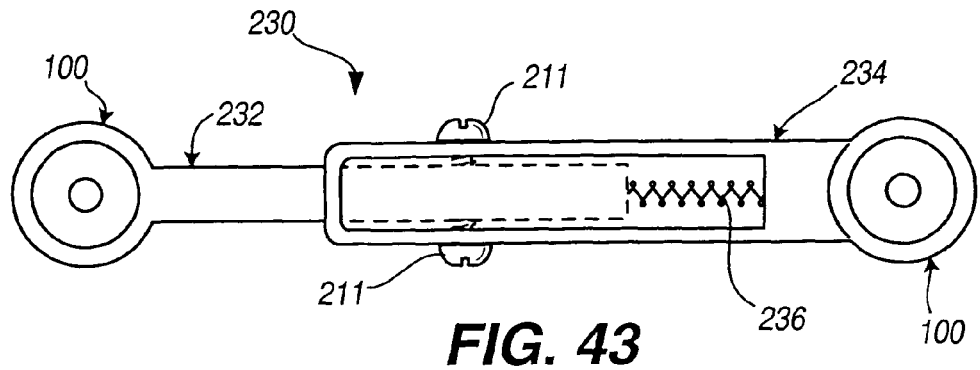
FIG. 43
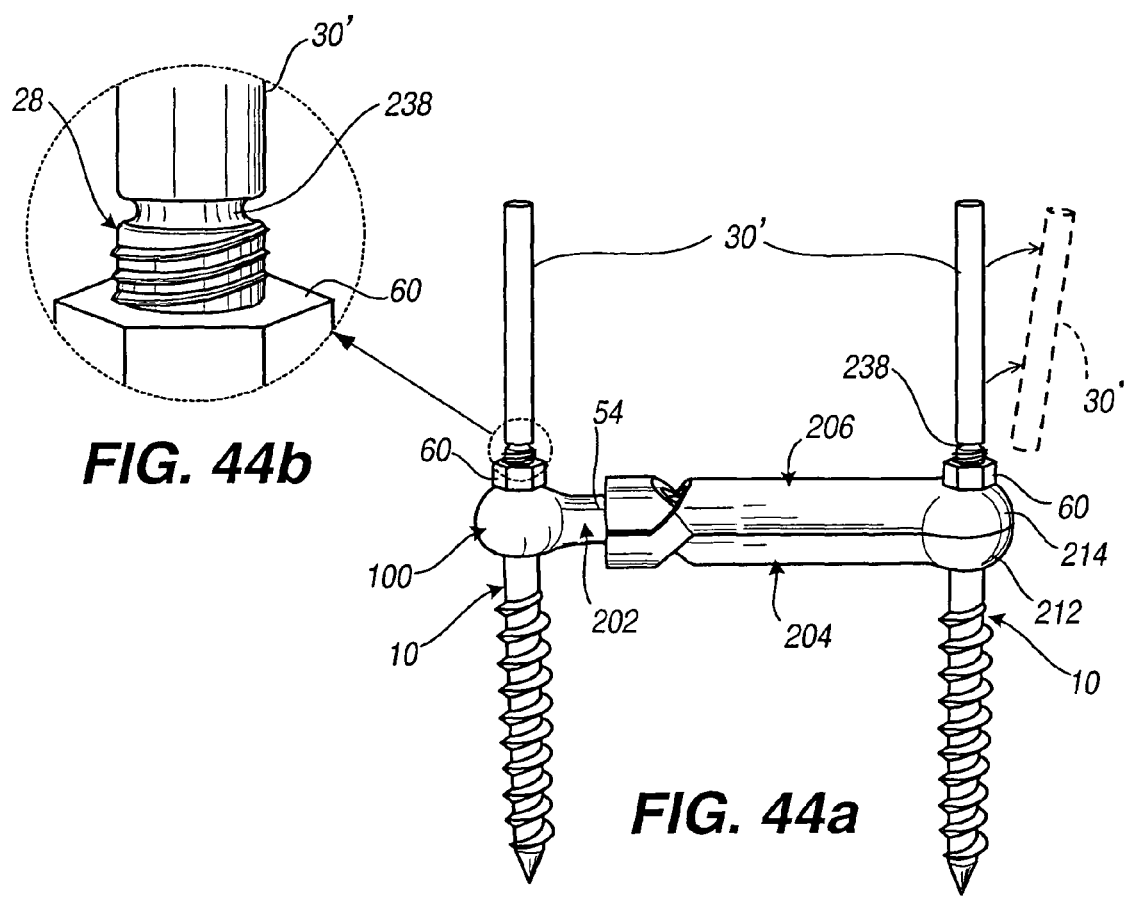
FIG. 44b
FIG. 44a

CONNECTION ROD FOR SCREW OR HOOK POLYAXIAL SYSTEM AND METHOD OF USE

CROSS-REFERENCE TO RELATED APPLICATIONS

This application is a divisional of U.S. patent application Ser. No. 10/262,574 filed on Sep. 30, 2002 and entitled "CONNECTION ROD FOR SCREW OR HOOK POLYAXIAL SYSTEM AND METHOD OF USE", which claimed priority from U.S. Provisional Patent Application No. 60/325,809 filed Sep. 28, 2001. The entire disclosures of these applications are considered to be part of the disclosure of the present application and are hereby incorporated by reference in their entirety.

FIELD OF THE INVENTION

This invention relates generally to an adjustable rod for stabilizing a portion of the spine, or two or more bone segments and a method of using the same. More specifically, the device and method include a series of components that provide a low-profile configuration when assembled, thereby minimizing tissue displacement and interference with nearby joint articulation.

BACKGROUND OF THE INVENTION

The use of fixation devices for the treatment of vertebrae deformities and injuries is well known in the art. Various fixation devices are used in medical treatment to correct curvatures and deformities, treat trauma and remedy various abnormal spinal conditions. Treatment of these conditions generally requires the implantation of various component pieces such as support rods, crosslinks, caudal facing hooks, cranial facing hooks and like components, which form a spinal implant system.

It is necessary in spinal implant systems to properly anchor the system to bone to provide necessary support of the implant. Bone screws are commonly used for anchoring spinal implant systems. However, there are several problems with the use of fixed screws for anchoring spinal implants. The exact final position of a bone screw is difficult, if not impossible, to predict prior to the exposure of the patient's bone. This unpredictability results from the uncertainty of exact bone formation and shape within an individual patient. Additionally, it can be difficult to predetermine the structure of the bone, i.e. whether the bone is soft or even osteoporotic. Even if the final position of the screw can be predetermined, the necessary shape and position of a spinal rod implant may create unwanted stress upon the bone screw or the bone itself. This is especially true where a plurality of screws is required along the spinal column for securement of an implant. The alignment of the rod with several screws along the vertebrae compounds this problem and makes undesired stress much more probable. Moreover, this misalignment may influence the extent and speed of correction of the spinal defect.

It is thus desirable to have a polyaxial securement method. There exists a number of patents drawn to polyaxial bone screws. Unfortunately, the advantage of many of these designs comes at the expense of bulk in the connection means or complexity of implantation. Such devices included complicated retention collets or securing systems that eliminate the device from functioning as a polyaxial system. In addition, as the size of a bone screw increases, so too does the displacement of normal bodily formations, such as muscular tissue or bone. It is common in the insertion of spinal implants to necessarily remove portions of vertebral bone to allow proper insertion of a bone screw. Moreover, this bulk may result in long-term muscular displacement that may lead to a patient's pain or discomfort.

Increased complexity of the installation procedure is undesirable because it increases a patient's time in surgery. Increased operating time is known to increase the risk of many complications associated with surgery. The additional time necessary to remove, or even temporarily dislocate, bone or muscular tissue also increases operating time, and thus the risk of complications.

In addition, the prior art fails to provide a low-profile multi-piece connector that includes poly-axial adjustability and that can be used to accommodate a variety of geometry requirements that may arise for certain patients. Therefore, a need exists to provide a low-profile multi-piece connector that can be adapted to a variety of geometry requirements.

The prior art also fails to provide a tool for implantation of an attachment device that has an entry channel for a tension link, or that otherwise has an expansion slot. Thus, a need exists for a tool that fittingly accepts the head of a attachment device that has a hollow core with either an entry channel and/or at least one expansion slot, and that can be used to accept and drive into bone the attachment device.

In addition to the above noted shortcomings of the prior art, the prior art also fails to provide a low-profile device that includes a connector that can be positioned at the very end of a stabilizing rod, thereby providing a device that does not disturb the adjacent vertebra. More specifically, the connectors of the prior art require attachment to the rod with a section of rod extending beyond the connector itself. Accordingly, a need exists to reduce or otherwise minimize the length of rod run-out beyond the end connector to prevent interference with the articulation of the neighboring vertebrae.

The prior art also fails to provide a low-profile device that allows the rod length to be easily adjusted during implantation with a minimal amount of effort by the installing surgeon. More particularly, where two bone segments, such as a first vertebra and a second vertebra, are being bridged by existing devices, the rod typically extends beyond the connector, and needs to be specifically chosen or otherwise cut to accommodate the dimensions of the subject patient. Therefore, a need exists to provide an adjustable length rod implantation assembly that can be installed relatively easily by a surgeon, and that further has an ability to be adjusted at the moment of implantation to thereby accommodate the geometry requirements of the patient. In addition, a need exists for an extended shaft to a tension link that can thereby act as a guide or leader for installation of a number of the assembly components. Such a device can serve to simply the installation process and minimize the size of the incision necessary to access the patient's interior surgical site.

The prior art also fails to provide a rod implant that can be telescopically adjusted at the time of implantation. Such a device is needed to further accommodate the individual patient's requirements that exist and that are encountered upon performing and incision and encountering in situ conditions.

It is also desirable with some patients to have a spinal implant system that allows the vertebral column to settle naturally under the weight of the human body. Human bone heals more readily under some pressure. In a rigid spinal implant system, the patient's spinal column may be unnaturally held apart by the structure of the implant. It is possible that this stretching of the vertebrae, in relation to one another, results in delayed or incomplete healing of the bone.

In view of the above, there is a long felt but unsolved need for a method and system that avoids the above-mentioned deficiencies of the prior art and that provides an effective system that is relatively simple to employ and requires minimal displacement or removal of bodily tissue.

SUMMARY OF THE INVENTION

In accordance with the present invention, a polyaxial attachment device is provided with a socket for receiving a headed connecting link. A surgical implant assembly employing the polyaxial attachment device is also disclosed. The surgical implant assembly of the present invention includes an attachment device, a headed anchor shaft (or tension link), a connector formed as an integral part of a first stabilizing rod, and a clamp device that grasps the first stabilizing rod while also attaching to a second attachment device using a second interconnecting mechanism, such as a tension link.

The attachment device of the present invention has a shank with a securement mechanism on one end and an enlarged area on the other end. The securement mechanism may be selected from any known method of securing one article to another, for example, a hook, a plate, a flanged device, or an adhesive, however, it is anticipated that the most common securement mechanism used will be screw threads. The enlarged area includes a hollow core, i.e., a socket, and a central aperture providing access to the hollow core. The enlarged area need only be large enough to envelop the head of the tension link and provide a wall thickness necessary for strength considerations.

The attachment device may include additional features to enable the insertion of the head end of the tension link into the hollow core. The enlarged area of the attachment device may include an entry channel leading to the hollow core that accommodates the tension link head end so that the tension link may be advanced, shaft end first, until the head of the tension link is positioned within the hollow core. Additionally, the entry channel and the central aperture may be connected by a slot through the wall of the enlarged area. In this way, the tension link head end may be positioned within the hollow core without extending the entire length of the tension link beyond the enlarged area of the attachment device opposite the central aperture. The surgeon may place only the head end of the tension link at the entry channel, slide the tension link shaft through the tension link slot, and draw the head end into the hollow core. Alternatively, in lieu of an entry channel or tension link slot, the enlarged area may include one or more expansion slots. In this embodiment, the head of the tension link may be inserted into the hollow core through the central aperture by the application of enough force to expand the central aperture. Once the head of the tension link is properly received into the hollow core, the enlarged area returns to its original size and shape. Unwanted expansion of the enlarged area is prevented by the connector once the enlarged area is properly seated into a head receptacle on the connector during implantation. This maintains the head of the tension link within the hollow core.

The external surface of the enlarged area of the attachment device may be formed into one of limitless geometries. For example, the external surface may be spherical, or at least semi-spherical. The external surface may be at least slightly aspheric. By controlling the degree of asphericity, the contact surface between the attachment device and the connector can thereby control the degree of freedom of the connector relative to the attachment device. Alternatively, the external surface may be conical, or a truncated cone shape, to allow rotational freedom while maintaining a coaxial relationship between the attachment device and the connector. Also, the external surface may be polyhedral or provided with facets to allow angular displacement in only finite steps or prevented altogether. In embodiments including conical, truncated cone shape, polyhedral or faceted geometries of the external surface of the enlarged area, the mating head receptacle of the connector may have corresponding geometry.

The tension link secures and maintains the position of the connector relative to the attachment device. The tension link is a shaft with a head end and a thread end. The head end, as described above, is contained within the hollow core of the attachment device. The threaded end extends through the connector and is secured to the connector by a tension link nut (herein also referred to as a "link nut") threaded onto the thread end.

The tension link may be provided with a projection to prevent undesirable rotation of the link when tightening or loosening the link nut, yet still enable angular displacement necessary to provide a polyaxial connection. In one embodiment, a link retainer, or a projection, may be provided on the shaft of the tension link. In this embodiment, it is necessary to provide a link retainer recess within the tension link cavity of the connector. In an alternative embodiment, the link retainer, or projection, may be provided at the intersection of the tension link shaft and the head end, and extending over a portion of the surface of the head end. In this embodiment, used with the attachment device embodiment including a tension link slot, the rotation may be prevented by contacting the link retainer with one side of the tension link slot. In either of the two foregoing embodiments, it is desirable to undersize the link retainer, relative to the link retainer recess or the tension link slot, so that the polyaxial freedom of the tension link and attachment device combination is not unduly limited. In an alternative embodiment, a retaining process, or small projection, may be provided on the tension link head. The retaining process should be positioned such that the retaining process is within the entry channel. Undesired rotation may be prevented by contacting the small projection with the wall of the entry channel.

The connector couples the attachment device to the implant component, such as a spinal rod implant. One type of connector described herein has a connecting end with a head receptacle, a rod end with a rod aperture, and a tension link cavity. The tension link, with its head positioned in the hollow core of the attachment device, is inserted through the tension link cavity so that an enlarged area of the attachment device nests in the head receptacle. The rod aperture secures the implant component in a desired position. The rod aperture may be secured by the tension link when the link nut is threaded and tightened on the link. In this embodiment, the rod end of the connector has a gap on one side of the rod aperture. The tension link cavity extends continuously through the tension link on both sides of the gap. The upper portion of the rod end forms a tab. As the tab is drawn toward the receiver end of the connector the gap narrows until the rod aperture firmly clamps the implant component or until the gap is drawn completely together.

In still other embodiments, it may also be desirable to provide a separate system for securing the connector to the attachment device and for securing the implant component to the connector. Therefore, in an alternative embodiment, the gap is connected to the rod aperture in a position that does not intersect the rod aperture. In this embodiment, a separate screw, or other connection device, is required to secure the implant component in the rod aperture. The tension link is then used to secure the connector to the attachment device.

In either of the two foregoing connector embodiments, it may be desirable to secure the rod within the rod aperture without clamping to the extent axial movement of the rod within the rod aperture is prevented. In this way, for example, the spine may settle under its own weight and provide a better healing environment for the bone. In conjunction with this embodiment, the implant component may be supplied with flanges, or other extensions to constrain axial movement of the implant component within a desired range.

To surgically implant a device of the present invention, the surgeon may attach an attachment device, selected from one of the embodiments of the present invention. After successful attachment, the surgeon may insert a tension link of the present invention by positioning the head end of the tension link within the hollow core of the attachment device. The surgeon may then place a connector, with a head receptacle designed for mating with the second end of the attachment device, upon the attachment device by inserting the tension link through the tension link cavity of the connector. At this point, the surgeon may select the desired angle of position of the connector for attaching a implant component. Once the connector is properly adjusted, the link nut may be secured to the tension link, thereby securing the elements together in the desired position. The link nut may be loosened, as necessary, to readjust the placement of the implant component. Alternatively, if a connector having a separate implant component securement device is used, the step of securing the link nut may be delayed until after the implant component is secured in the rod aperture and properly positioned.

Based on the foregoing summary, a number of worthwhile aspects of the present invention can be readily identified. An attachment device is provided with a small and simple polyaxial adjustment mechanism. The minimal size of the enlarged area of the attachment device allows attachment of the device to human bone without significant displacement of human tissue. Therefore, the complexity of surgery and the following pain and discomfort of the patient may be minimized. The polyaxial nature of the device, combined with the small size, may allow a surgeon to attach the securement device to a secure portion of the human body without the need to remove bony processes to accommodate a larger attachment device. Additionally, a simple surgical implant assembly, including the polyaxial attachment device, is provided. The simplicity of the elements, and the assembly process thereof, may reduce the patient's time in surgery, thus reducing the risk and probability of surgical complications. Finally, a number of embodiments of the present invention may be used in combination to allow the surgeon great latitude in selection of materials. The surgeon may select from different embodiments of the attachment device, the tension link, and the connector to best fit the surgical implant parameters. With these choices the surgeon may then best determine which embodiments of which elements to select to minimize removal or displacement of bodily tissue or bone, and thereby reduce both the patient's risk of surgical complications and post-surgical pain and discomfort.

A significant feature of the present invention is the ability to provide a construct used to stabilize the spine or a portion thereof. The construct utilizes a single tension link nut to tighten down the structure at each bone screw (also referred to herein as an attachment device) location. More particularly, the present invention utilizes a bone screw or attachment device that possesses threads at one end along a shaft and an enlarged head with a hollow core at the other end. The threads are used to secure the bone screw to bone. The enlarged head of the bone screw includes an entry channel, tension link slot, or both that allows the shaft of the tension link to be fed up through the entry channel or tension link slot. In addition, the hollow core is shaped to receive the head of a tension link. The enlarged area of the bone screw possesses an aperture that is sized to permit the shaft of the tension link to pass through it, while retaining the head of the tension link. The shaft of the tension link is then fed through a connector. The connector is a component that possesses a separate aperture to receive a stabilizing rod. A tension link nut is then secured to the end of the threaded tension link shaft, thereby securing the connector to the tension link and bone screw.

In a separate aspect of the invention, a tool is provided to insert the attachment device. The tool includes a head portion that cooperates with the structural features of the attachment device. More specifically, the head portion of the tool includes a projection to mate with the hollow core, and/or the expansion slot, and/or the entry channel of the attachment device. The tool is rotated to force the threads of the opposite end of the attachment device to advance into the target bone segment. After the attachment device is inserted, the tool is disengaged from the attachment device thereby leaving the attachment device installed.

In an another embodiment of the invention, a multi-piece connector is provided that allows additional adjustability of the connector device. The multi-piece connector includes use of the attachment device having a hollow core and a tension link that includes a head that is fitted into the hollow core. A first piece of the multi-piece connect is attached by feeding the shaft of the tension link through an opening in the first piece. The implant rod is then positioned proximate the first piece and adjacent a cam portion of the first piece. The second piece of the multi-piece connector is then positioned over the implant rod by again passing the shaft of the tension link through an opening in the second piece. Finally, after adjusting the desired angle of the multi-piece connector by rotating the tension link within the attachment device, a link nut is then applied to the threaded end of the shaft of the tension link thereby tightening the nut against the connector and the enlarged head of the attachment device.

In an alternate embodiment, a connector is formed in the implant rod itself. In this embodiment, the rod possesses a receptacle that is a socket, such that the ball of the enlarged area of the attachment device with the head of the tension link in place, fits into the socket that is an integral part of the rod. Thus, a ball-and-socket arrangement is formed providing a polyaxial connector within the rod itself. A tension link nut is then secured to the end of the threaded shaft of the tension link, thereby securing the rod to the bone screw. When positioned at the end of a rod, this is a very low profile configuration that minimizes the length of the incision that is necessary to perform the surgery. Furthermore, a mechanical advantage is gained by the interaction of the components as previously described. Specifically, strength of the final connection is not simply attributable to the tightening of the tension link nut, but is also attributable, in part, to the placement of the head of the tension link within the hollow core of the bone screw, or attachment device. In so doing, the head of the tension link causes a slight expansion of the hollow core, much like how a wedge is used to secure an axe head at the top of an axe handle. The enlarged area of the screw is in turn partially encompassed by the receptacle socket of the rod itself.

In yet a separate aspect of the invention, a clamp device is furnished for providing an adjustable rod structure for implantation. In one embodiment of the clamp, the clamp includes a lower clamp portion and an upper clamp portion. The lower clamp portion has a clamp region that cooperates with a clamp region on the upper clamp portion. At a spaced distance from the clamp regions, the lower clamp portion has a securing end that cooperates with a securing end on the upper clamp portion. The lower and upper clamp portions are used in combination with an interior rod member that is grasped by the clamp regions of the lower and upper clamp portions when the securing ends of the lower and upper clamp portions are brought into a tight mating configuration. More specifically, the securing ends of the lower and upper clamp portions include receptacles that have sockets that mate with each other and that also mate with the enlarged area of an attachment device.

A method of use is also presented for the clamp device, wherein in a preferred embodiment the two attachment devices are installed by advancing an attachment device into each of two bone segments. The hollow core of each attachment device is then fitted with a the head of a tension link. Alternately, the tension link may be inserted into the hollow core of the tension link prior to insertion of the attachment devices into bone. After the attachment devices with their respective tension links are in place, one of the attachment devices is fitted with an interior rod member that includes a rod portion and an end connector in the form of a receptacle shaped like a socket. The socket includes a tension link cavity such that the shaft of the tension link is passed through the tension link cavity as the socket is being placed over the enlarged area of the first attachment device. A clamp comprising a lower and upper clamp portion is then assembled to grasp the rod portion of the interior rod member as the upper and lower clamp are connected to the second attachment device by passing the shaft of the second tension link through tension link cavities in the securing ends of the lower and upper clamp portions. Link nuts are then threaded on to exposed ends of the tension link shafts and are tightened. The position of the interior rod member can be adjusted within the clamp as the link nuts are tightened, thereby allowing the surgeon to adjust the size of the assembly to accommodate the patient's needs for a customized fit. The assembly minimizes the need to create a large incision because implantation work can be substantially performed from a direction perpendicular to the bone segments. Furthermore, this low profile assembly is relatively simple to install, thereby reducing surgery time over existing stabilizing devices.

In a separate aspect of the invention, a telescoping rod is provided that allows adjustability of the rod. The telescoping rod includes an inner and an outer member that cooperate to allow the surgeon to adjust the length of the rod to span two attachment devices. A set screw may be used with this embodiment to interlock the inner and the outer rod members.

In yet a separate aspect of the invention, the tension links may include an extended shaft that serve as guides for lowering and/or installing implantation components over and onto the attachment devices. After acting as guides for the lowering of implantation components over the attachment devices, link nuts are guided to the thread portions of the tension links. The extended shafts are subsequently removed by a shearing tool, by breaking the extended shaft portion away from the tension link along a pre-existing score location, or by other appropriate means.

Additional advantages of the present invention will become readily apparent from the following discussion, particularly when taken together with the accompanying drawings.

BRIEF DESCRIPTION OF THE DRAWINGS

FIG. 1a is a partial cross-sectional view of one embodiment of the attachment device of the present invention;

FIG. 1b is an end perspective view of an alternative embodiment of the attachment device of the present invention;

FIG. 2 is an end perspective view of an alternative embodiment of the attachment device of the present invention;

FIG. 3 is a cross-sectional view of the attachment device shown if FIG. 2;

FIG. 9b is a side elevation view of the tension link with link retainer shown in FIG. 9a;

FIG. 9c is an end view of the tension link with link retainer shown in FIG. 9a;

FIG. 10b is a side elevation view of the tension link with link retainer shown in FIG. 10a;

FIG. 16 is a side elevation view of yet another alternative embodiment of the connector of the present invention;

FIG. 17 is a cross-sectional view of one embodiment of the surgical implant assembly of the present invention;

FIG. 18 is a perspective view of an alternative embodiment of the surgical implant assembly of the present invention;

FIG. 19b is a plan view of the surgical implant assembly shown in FIG. 19a;

FIG. 29 is a perspective view of the connector shown in FIG. 25 with the connector shown in combination with an attachment device and a tension link;

FIG. 30 is an end cross-sectional view of the combination of structures shown in FIG. 29;

FIG. 31 is a perspective view of a separate aspect of the invention comprising a clamp, wherein the clamp is depicted as a component of a stabilization assembly;

FIG. 38 is a partially exploded perspective view of two stabilization assemblies including clamps, wherein the assemblies are aligned for implantation into two vertebra;

FIG. 39 is a side elevation view of one stabilization assembly including a clamp device after implantation into two vertebra;

FIG. 40b is a cross-sectional view taken along line 40b-40b shown in FIG. 40a;

FIG. 42b is a cross-sectional view taken along line 42b-42b shown in FIG. 42a;

FIG. 42c is a cross-sectional view taken along line 42c-42c shown in FIG. 42a;

FIG. 43 is a plan view of a separate aspect of the invention;

FIG. 44a is a perspective view of an stabilization assembly having extended tension link shafts; and FIG. 44b is an enlarged detail view of an aspect of an extended tension link shaft shown in FIG. 44a.

Figure 4:
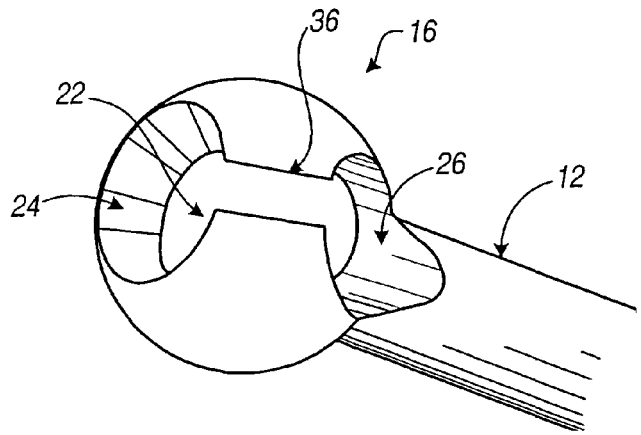
FIG. 4 is an end perspective view of another alternative embodiment of the attachment device of the present invention.

While the following disclosure describes the invention in connection with those embodiments presented, one should understand that the invention is not strictly limited to these embodiments. Furthermore, one should understand that the drawings are not necessarily to scale, and that in certain instances, the disclosure may not include details which are not necessary for an understanding of the present invention, such as conventional details of fabrication.

DETAILED DESCRIPTION OF THE PREFERRED EMBODIMENT

With reference to FIG. 1, one embodiment of the attachment device (or connection device) of the present invention is shown in partial cross-section. The attachment device 10 includes a shank 12 having a first end 14 and a second end 16.

The first end 14 of the shank 12 includes a securement mechanism 18. As shown in FIG. 1, the securement mechanism 18 may be screw threads. It is noted, however, that the securement mechanism 18 may include any known method of securing one item to another. For example, the securement mechanism 18 may be a hook, a plate, a flange, or adhesive. In the case of the securement mechanism 18 as a flange or plate, the securement mechanism 18 may require additional hardware such as screws, bolts, or adhesive to secure the plate or flange to the intended object. In the case of the securement mechanism 18 as an adhesive, or requiring the additional use of adhesive, the adhesive would necessarily be applied to the securement mechanism 18, not included within it. Additionally, adhesive could be used with the securement mechanism 18, e.g., applied to screw threads, for additional securement capacity.

The second end 16 of the shank 12 generally comprises an enlarged area 20 including a central core 22 and an aperture 24. The second end 16 of FIG. 1 is shown in cross-sectional view to more clearly show the central core 22 and the aperture 24.

With reference to FIG. 2, an embodiment of the second end 16 of the shank 12 is shown. In this embodiment, the enlarged area 20 includes a hollow core 22 and a central aperture 24. The enlarged area also includes an entry channel 26. The entry channel 26 is operatively connected with the hollow core 22 such that a tension link 28, having a shaft 30 with a threaded end 32 and a head end 34, may be inserted, threaded end 32 first, through the entry channel 26, the hollow core 22, and central aperture 24 until the head end 34 of the tension link 28 is retained within the hollow core 22 by the central aperture 24.

With reference to FIG. 3, the embodiment of the second end 16 of attachment device 10 is shown in cross-section. FIG. 3 clarifies the operational relationship between the entry channel 26, the hollow core 22 and the central aperture 24.

With reference to FIG. 4, an alternative embodiment of the attachment device 10 is shown. This embodiment is similar to the embodiment of FIGS. 2 and 3, but with an additional element. In this embodiment, a tension link slot 36 is provided between the entry channel 26 and the central aperture 24. The tension link slot 36 allows the shaft 30 of the tension link 28 to be inserted through the tension link slot 36. In this way, the tension link 28 may be inserted through the tension link slot 36 to pass through both central aperture 24 and the entry channel 26. The tension link 28 may then be drawn through the aperture 24 until the tension link head end 34 passes through the entry channel 26 and rests in the hollow core 22. This embodiment may allow the surgeon to insert a tension link 28 into an attachment device 10 secured to the human body in cases where the obstacles, including the human body itself, or parts thereof, prevent the length of the tension link 28 from extending completely beyond the entry channel 26 opposite the central aperture 24.

Figure 5:
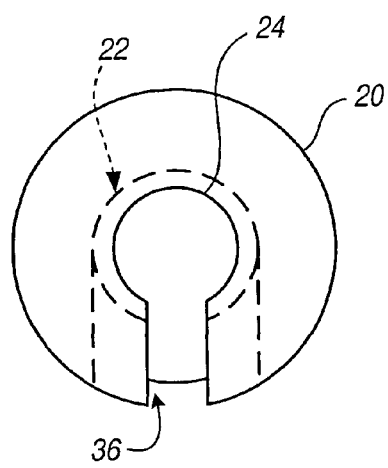
FIG. 5 is a top plan view of the attachment device shown in FIG. 4.

FIG. 5 shows an end view, from the second end 16, of the embodiment of the attachment device 10 from FIG. 4. FIG. 5 clarifies the relationship between the tension link slot 36 and the central aperture 24, the hollow core 22 and the entry channel 26. It should be noted that the central aperture 24 is shown in FIG. 5 as located at top, dead center of the enlarged portion 20 of the attachment device 10. However, the location of the central aperture 24 may be at any angular relationship to the shank 12. This location of the central aperture 24 applies to this, and every other, embodiment of the attachment device 10. The hollow core 22 should be sized to receive the head end 34 of the tension link 28, in this and other embodiments of the present invention. Similarly, the central aperture 24 should be sized to accommodate the tension link shaft 30, and with enough clearance to provide the desired angular displacement. For example, it may be desirable to provide from about 0 to 60 degrees of angular displacement of the tension link 28 from the longitudinal axis of the attachment device 10. In some instances, a smaller range may be advantageous.

Figure 6:
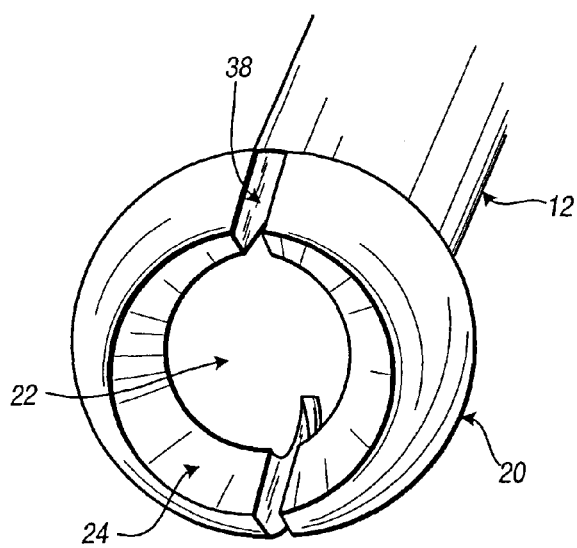
FIG. 6 is an end perspective view of yet another alternative embodiment of the attachment device of the present invention.

With reference to FIG. 6, an additional alternative embodiment of the enlarged area 20 of the attachment device 10 is shown. In this embodiment, the enlarged area 20 includes a hollow core 22 and a central aperture 24, but does not include an entry channel 26. Instead, at least one expansion slot 38 extends from the central aperture 24 along the exterior surface of the enlarged area 20. The expansion slot 38 extends completely through the wall defined by the hollow core 22 and the exterior surface of the enlarged area 20. The embodiment of FIG. 6 includes two expansion slots 38 diametrically opposite from one another, however, the number of expansion slots 38 and their location in radial relation to the central aperture 24 may be selected in the design of the attachment device 10 according to, among other things, the application, or the size and material of construction of the attachment device 10. The expansion slot(s) 38 may allow insertion of the head end 34 of the tension link 28 into the hollow core 22 through the central aperture 24 by allowing deformation of the enlarged area 20. As explained in more detail below, the connector 40, more specifically, the head receptacle 42 of the connector 40, when properly installed over the enlarged area 20 prevents further deformation of the enlarged area 20, and thus the central aperture 24 retains the head 34 of the tension link 28 within the hollow core 22.

Figure 7:
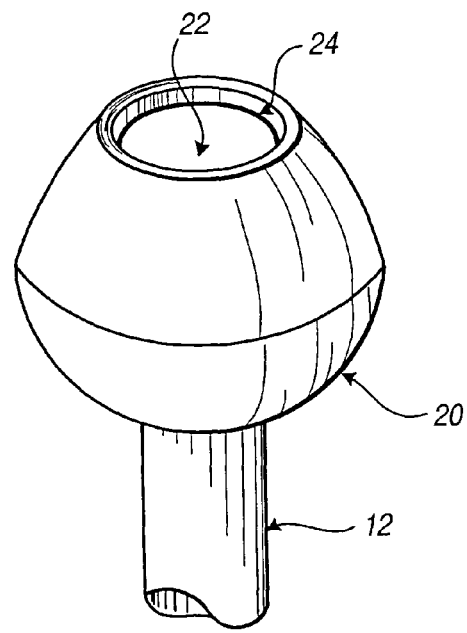
FIG. 7 is an end perspective view of still another alternative embodiment of the attachment device of the present invention.

With reference to FIG. 7, yet another alternative embodiment of the enlarged area 20 of the attachment device 10 is shown. In this embodiment, at least a portion of the enlarged area 20 includes a substantially conical portion around the central aperture 24. The head receptacle 42 of the connector 40 has mating geometry to the enlarged area 20. Thus, the partially conical shape of the enlarged area 20 allows polyaxial positioning of the connector 40 while controlling movement in one degree of freedom. The connector 40 may rotate around the central axis of the conical section, however, the mating geometry of the head receptacle 42 prevents angular displacement relative to the central axis of the conical section. Obviously, the central aperture 24 may require that the shape of the enlarged area 20 not be truly conical. The central aperture 24 may necessitate the geometry of the enlarged area 20 to be more aptly described as a truncated cone shape.

Figure 8:
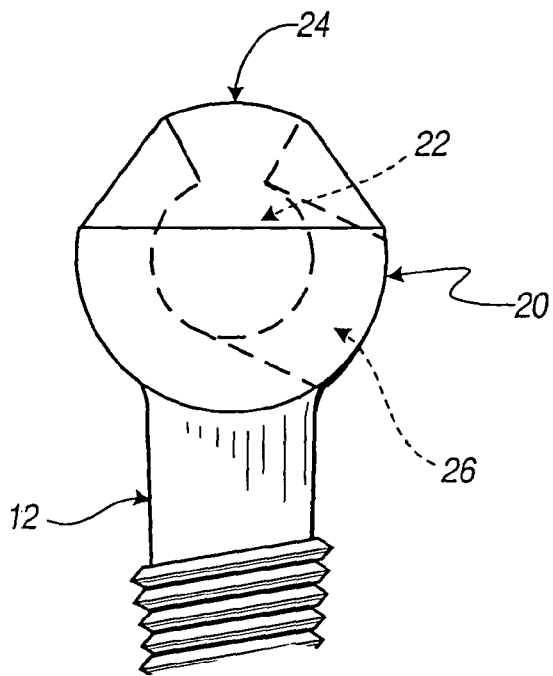
FIG. 8 is an elevation view of the attachment device shown in FIG. 7.

FIG. 8 shows the embodiment of the attachment device 10 of FIG. 7 in an elevation view. While FIG. 8 shows the enlarged area 20 to include a hollow core 22, a central aperture 24, and an entry channel 26, it is noted that conical-shaped enlarged area 20 shown in FIGS. 7 and 8 may be used with any alternative embodiments of the attachment device 10 related to the method of insertion of the tension link head 34 into the hollow core 22, including, for example, the expansion slot(s) 38, or the tension link slot 36.

In alternative embodiments not shown in the drawings, the exterior surface of the enlarged area 20 may include other configurations. For example, the exterior surface of the enlarged area 20 may be formed as a polyhedron, such as a dodecahedron, or be provided with facets. In this embodiment, the head receptacle 42 of the connector 40 will also have a corresponding geometry. In this way, a polyaxial relationship is provided between the attachment device 10 and the connector 40, yet limiting this polyaxial relationship to a finite number of angular displacement.

The enlarged area 20 is shown in the drawings as at least approximately spheric. It is noted, however that the enlarged area 20 and/or the head receptacle 42 of the connector 40 may also be aspheric. The use of the aspheric construction of either the enlarged area 20 or the head receptacle 42, or both, may accommodate the elasticity and deformation of the material the structure. The amount of asphericity may be selected to control the area of surface contact between the enlarged area 20 and the head receptacle 42 of the connector 40. The amount of asphericity may also be selected to control or vary the degree of freedom required by the linkage.

Further, in any embodiment or configuration of the enlarged area 20, the external surface of the enlarged area 20 may be textured, i.e., provided with a specified surface roughness. The texture, or surface roughness, of the enlarged area 20 may be selected to properly control the friction between the enlarged area 20 and the head receptacle 42, and thus controlling, among other things, the tension force required to secure the devices together or degrees of freedom in their combination. It should be noted that the internal wall of the hollow core 22, the head end 34 of the tension link 28, and/or the head receptacle 42 of the connector 40 may also be provided with a texture, or surface roughness.

Figure 9A:
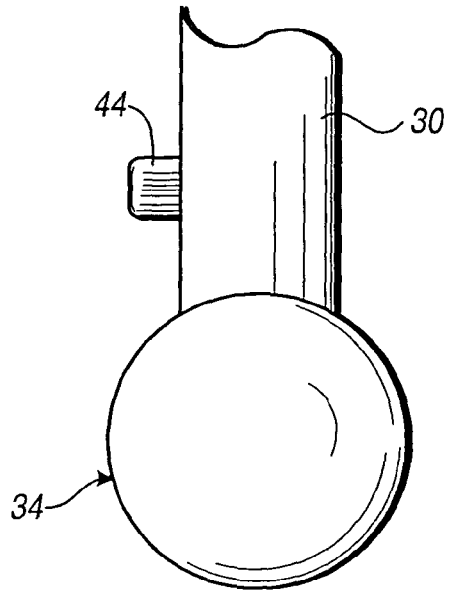
FIG. 9a is an front elevation view of one embodiment of the tension link with a link retainer of the present invention.
Figure 9B:
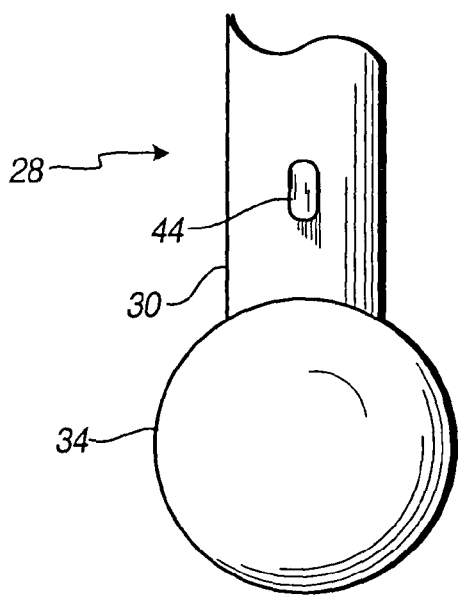
Figure 9C:
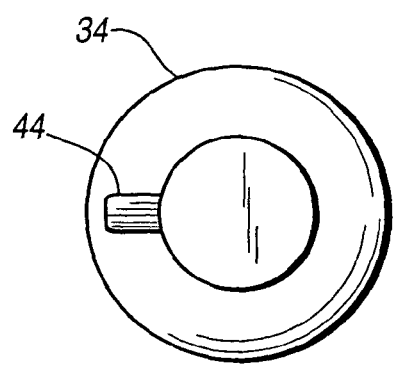

With reference to FIGS. 9a, 9b, and 9c, a tension link 28 is shown. The tension link 28 is generally a shaft 30 with a head end 34 and a thread end 32. As shown in FIGS. 9a, 9b, and 9c, one embodiment of the tension link 28 may include a link retainer 44. The link retainer 44, in this embodiment, comprises a projection on the shaft 30 of the tension link 28. The link retainer 44 may be used to prevent unwanted rotation, but not angular orientation, of the tension link 28 within the hollow core 22 of the attachment device 10. An extended tension link 28 is shown in FIG. 44, as will be discussed below.

FIG. 9a shows an embodiment of the tension link with a link retainer 44 in partial side elevation. FIG. 9b shows the same embodiment in front elevation. FIG. 9c shows this embodiment in plan view as seen from the thread end 32 of the tension link 28. The thread end 32 of the tension link 28 is not shown in FIGS. 9a, 9b, and 9c.

Figure 10A:
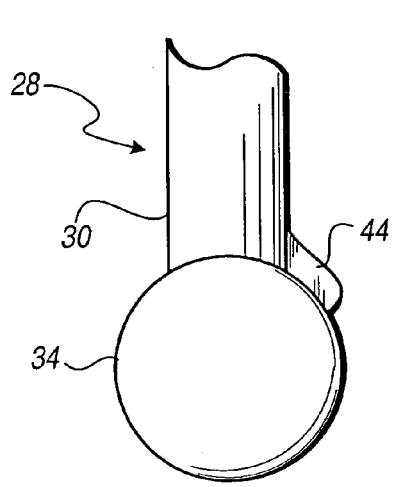
FIG. 10a is an front elevation view of an alternative embodiment of the tension link with a link retainer of the present invention.
Figure 10B:
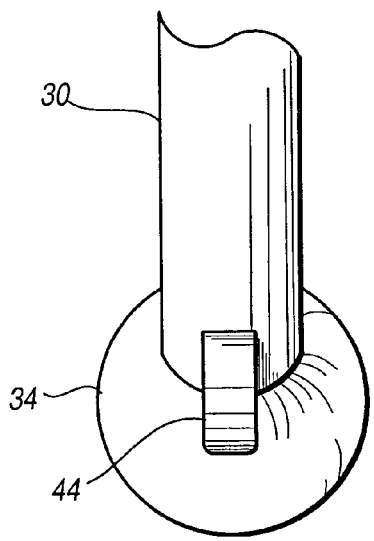

With reference to FIGS. 10a and 10b, an alternative embodiment of the link retainer 44 of the tension link 28 is shown. The tension link 28 is shown in partial side elevation and partial front elevation, in FIG. 10a and FIG. 10b, respectively. Again, this view is "partial" because the thread end 32 of the tension link 28 is omitted from the drawing. The link retainer 44 in this embodiment is a projection that spans the intersection of the shaft 30 and the head end 34 of the tension link 28 and extends partially along the surface of the head end 34. This embodiment may be used in conjunction with the embodiment of the attachment device 10 including the tension link slot 36, as shown in FIGS. 4 and 5 above. As in the previous embodiment, the tension link may be prevented from unwanted rotation of the tension link 28 within the hollow core 22. The link retainer 44 may be placed in contact with the wall of the tension link slot 36 to prevent such rotation.

Figure 11:
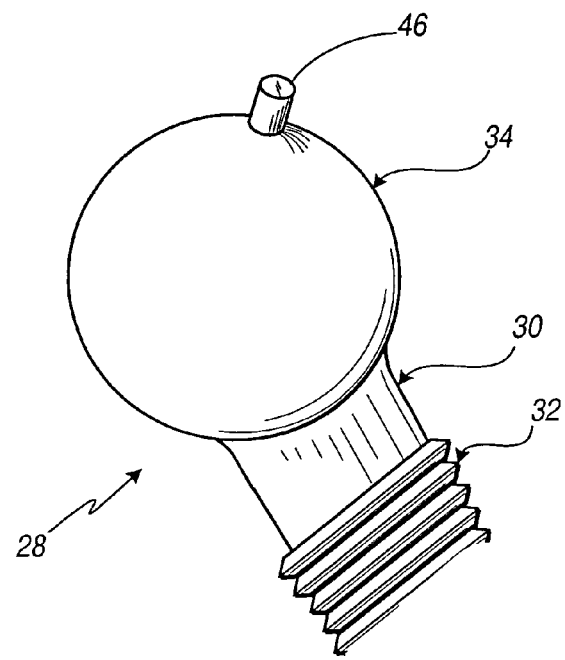
FIG. 11 is a perspective view of the tension link with head end process of the present invention.

With reference to FIG. 11, an alternative embodiment of the tension link 28 is shown. The tension link 28 again includes a shaft 30 with a head end 34 and a thread end 32, and, in this embodiment, a head end process 46. The head end process 46 is a projection on the head end 34 of the tension link 28. The head end process 46 may be used to prevent rotation of the tension link 28 within the hollow core 22 similar to the link retainer 44. However, this embodiment would most commonly be used with an attachment device 10 having a entry channel 26, and the head end process 46 could be placed in contact with a wall of the entry channel 26 to prevent the rotation.

Figure 12:
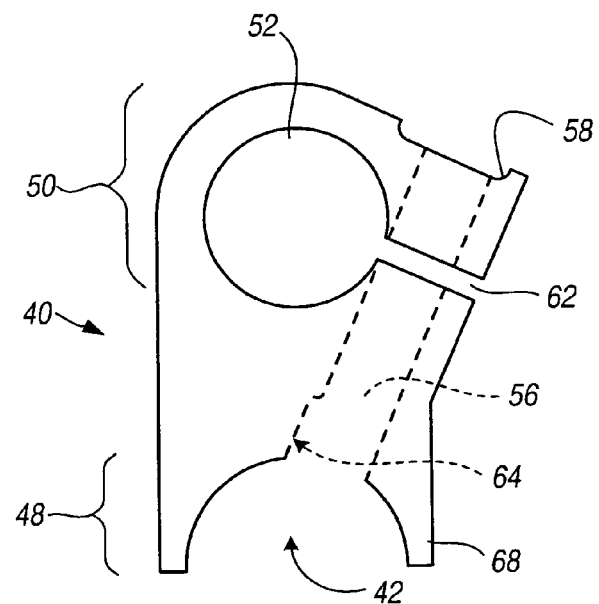
FIG. 12 is a side elevation view of one embodiment of the connector of the present invention.

With reference to FIG. 12, an embodiment of the connector 40 is shown. The connector has a receiving end 48 and a rod end 50. The receiving end 48 includes a head receptacle 42 for receiving the enlarged area 20 of the attachment device 10. The rod end 50 includes a rod aperture 52 for receiving a implant component 54, such as a spinal rod implant or other device. A tension link cavity 56 is provided from the head receptacle 42 to the rod end 50. The tension link cavity 56 is sized to allow the insertion of the thread end 32 of a tension link 28 through the connector 40. In the embodiment of the connector 40 shown in FIG. 12, a link nut recess 58 is provided at the rod end 50 adjacent to the tension link cavity 56 for seating a link nut 60 used to secure the connector 40 to the tension link 28. As shown in FIG. 12, the connector may include a gap 62 located medially between the receiving end 48 and the rod end 50, and in operative relationship with the rod aperture 52 such that when the gap 62 is closed, the rod aperture 52 may secure the implant component 54. In this embodiment, tightening of the link nut 60 on the tension link 28 closes the gap 62, and thus secures the implant component 54, concurrently with securing the connector 40 to the attachment device 10 in a desired position. The embodiment shown in FIG. 12 includes the alternative feature of a link retainer recess 64. The link retainer recess 64 is a void located along the tension link cavity 56 and adjacent to the head receptacle 42. The link retainer recess 64 accommodates the link retainer 44 of the embodiment shown in FIGS. 9a, 9b and 9c, such that the link retainer 44 may contact the wall of the link retainer recess 64 and prevent undesired rotation of the tension link 28. The link retainer recess 64 should be sized accordingly.

Figure 13:
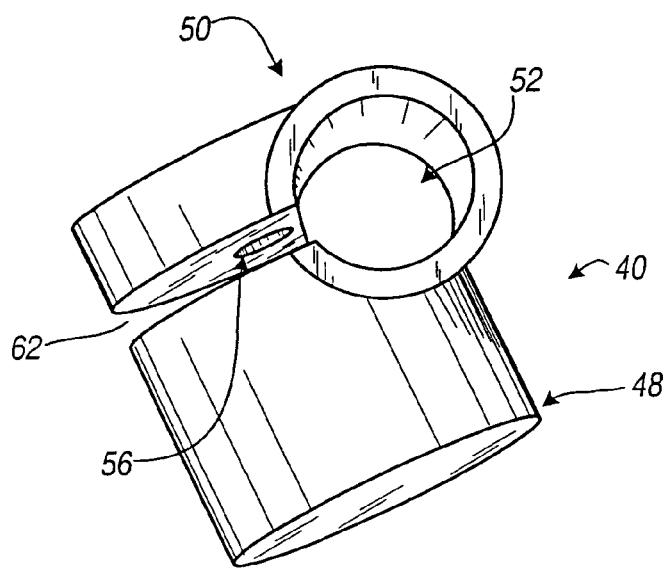
FIG. 13 is a side perspective view of an alternative embodiment of the connector of the present invention.

Referring now to FIG. 13, an alternative embodiment of the connector 40 of the present invention is shown. Like the embodiment of FIG. 13, the connector 40 of this embodiment has a receiving end 48 with a head receptacle 42, a rod end 50 with a rod aperture 52, and a tension link cavity 56. In this embodiment, however, the rod aperture 52 is offset from the body of the connector 40. The ability to offset the rod aperture 52 may provide greater latitude to the surgeon when attempting to avoid obstacles such as bones or other tissues.

Figure 14:
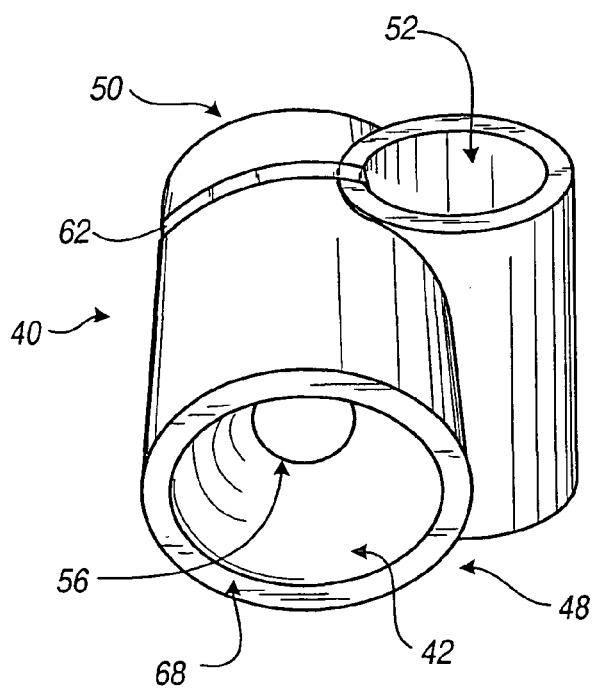
FIG. 14 is an bottom perspective view of the connector shown in FIG. 11.

FIG. 14 shows the embodiment of the connector 40 of FIG. 13 from the receiving end 48. The tension link cavity 56 in this embodiment does not include the alternative element of the link retainer recess 64.

Figure 15:
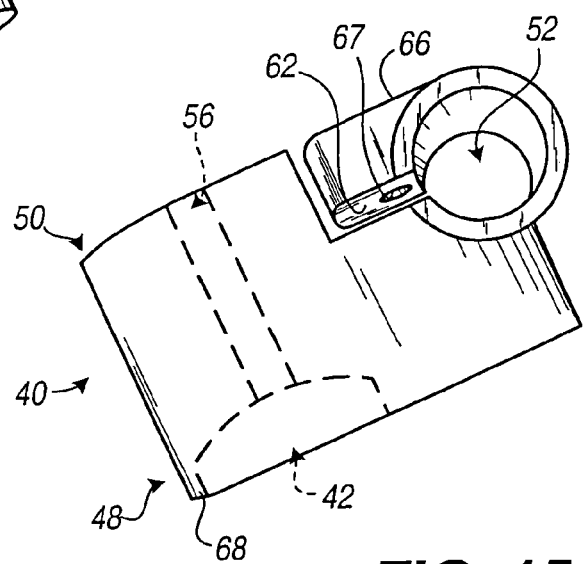
FIG. 15 is a side perspective view of another alternative embodiment of the connector of the present invention.

With reference to FIG. 15, an alternative embodiment of the connector 40 is shown. In this embodiment, the implant component 54 is secured in the rod aperture 52 separately from securing the connector 40 to the attachment device 10 by the tension link 28. The tension link cavity 56 does not intersect the gap 62 in the wall of the rod aperture 52. Instead, a portion of the wall of the rod aperture forms a tab 66 with a implant securement hole 67. The tab 66 may be secured to the connector 40 by an implant securement screw 69 inserted through the implant securement hole 67 and into the connector 40. This configuration may provide further offset capacity for the connector from the attachment device 10.

Referring now to FIG. 16, a further embodiment of the connector 40 is provided wherein the implant component 54 is secured in the rod aperture 52 separately from securing the connector 40 to the attachment device 10. As in the embodiment of FIG. 15, a portion of the wall of the rod aperture forms a tab 66 with a implant securement hole 67. The tab 66 may be secured to the connector 40 by an implant securement screw 69 inserted through the implant securement hole 67 and into the connector 40. However, in this embodiment, the tab 66 is located toward the exterior of the connector 40.

With reference to FIG. 17, a possible combination of the above described elements is provided to show a surgical implantation system. The surgical implant system 70 includes an attachment device 10, a tension link 28, a connector 40, and a link nut 60. The implant component 54 is omitted from this drawing. The tension link head end 34 is inserted into the hollow core 22 of the attachment device 10. The tension link 28 extends through the tension link cavity 56 of the connector 40 such that the enlarged area 20 of the attachment device 10 is received into the head receptacle 42 of the connector 40. The connector 40 may then be secured to the attachment device 10 in proper position by tightening the link nut 60 on the tension link 28. In this embodiment, tightening the link nut 60 will also close the rod aperture gap 62 and secure the implant component 54 within the rod aperture 52.

As an aside, the head receptacle wall 68 is shown extending to approximately the "equator" or diameter of the enlarged area 20 of the attachment device 10. It should be noted that the extent that the head receptacle wall 68 engages the enlarged area 20 may be varied. For instance, a smaller wall 68 engagement may be desirable to increase the polyaxial adjustment of the assembly. Alternatively, it may be desirable to provide greater wall 68 engagement with the enlarged area 20 to prevent unnecessary deformation of the enlarged area 20, for example when the enlarged area 20 is provided with an expansion slot 38 or a tension link slot 36. Further, if the head receptacle wall 68 is designed for engagement beyond the "equator" of the enlarged area, the head receptacle wall 68 may match the contour of the enlarged area 20. In other words, the size of the head receptacle 42, at the farthest point on the receiving end 48 of the connector 40, may be smaller than the maximum size of the enlarged area 20 at its "equator." This may provide an additional advantage to the surgeon. In this situation, a tactile or audible signal may be provided when the enlarged area 20 is properly received into the head receptacle 42.

With reference to FIG. 18, an alternative arrangement of the surgical implant system 70 is shown. In this embodiment, the connectors 40 secure a implant component 54, in this case a rod, to the attachment devices 10. The orientation of the attachment devices 10 illustrate the polyaxial nature of the system 70. The attachment devices may be secured to whatever structure is necessary at different angles and on different planes.

Figure 19A:
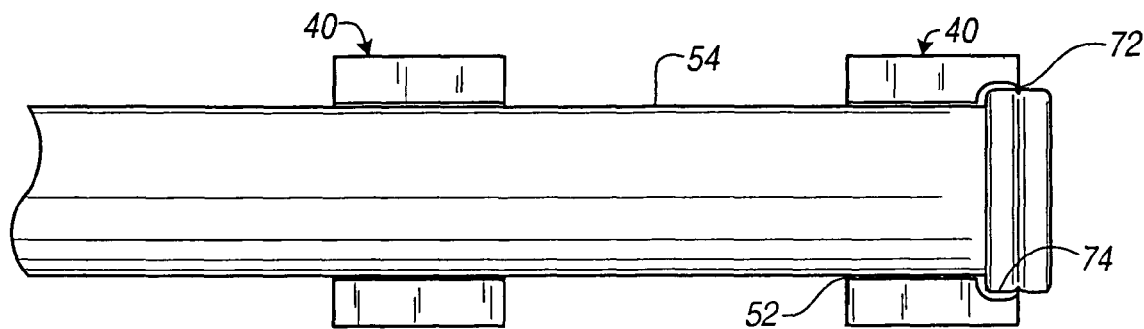
FIG. 19a is a cross-sectional elevation view of another alternative embodiment of the surgical implant assembly of the present invention.
Figure 19B:
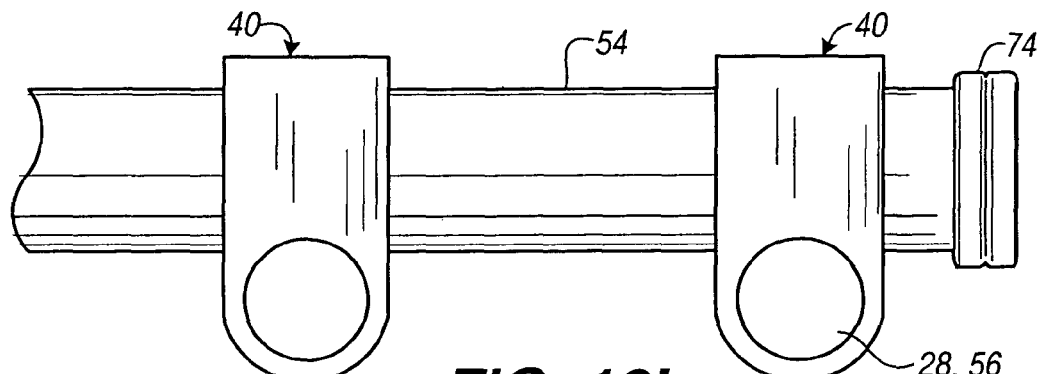

Referring now to FIGS. 19a and 19b, an alternative embodiment of the surgical implantation system 70 is provided. In this embodiment, a dynamic system is created wherein the implant component 54 is allowed to move freely along its longitudinal axis within connector rod aperture 52. This is accomplished by manufacturing some clearance tolerance within the rod aperture 52 when the link nut 60 is completely tightened on tension link 28. FIG. 19a also shows an alternative embodiment of a retaining recess 72 adjacent to the connector rod aperture 52. The retaining recess 72 corresponds with a retaining process 74 on the implant component 54 to limit the extent of dynamic nature within the implant. The retaining recess 72 and the retaining process 74 are sized and work in relation to one another such that the longitudinal movement of the implant component 54 is arrested when the retaining process 74 nests in the retaining recess 72.

Although it is not shown in the drawings, it is also possible to use the retaining process 74 without the retaining recess 72. It this aspect, the longitudinal movement of the implant component 54 is arrested when the retaining process 74 contacts the exterior surface of the connector 40 at the rod aperture 52.

It is also possible to use either of the two above embodiments on either side of the rod aperture 52, wherein the longitudinal movement of the implant component 54 can be constrained in one or both directions.

Additional embodiments of the present invention are not shown in the drawings. For example, it is expected that the attachment device 10 may be used in conjunction with a hook in place of the tension link 28. In this embodiment, the hook would have a ball end and a hook end. The ball end would be inserted into the central core 22 of the attachment device 10 and the hook end would be used to secure some bodily structure, such as a bone. The hook rod would be capable of polyaxial movement.

The present invention also relates to a method of using the embodiments as set forth above. In one embodiment, the method using a surgical implant system 70 would first require the selective insertion of the attachment device 10 into a human bone. The tension link head end 34 could then inserted into the hollow core 22 of the attachment device 10. The step of insertion of the head end 34 would depend upon the embodiment of the attachment device 10 selected. For example, if an attachment device 10 with an entry channel 26, but no tension link slot 36, is provided, the tension link 28 is positioned in the aperture 24 by way of the entry channel 26. The connector 40 is positioned on the tension link 28 by inserting the tension link 28 through the connector tension link cavity 56.

At this point, the surgeon can position the connector 40 such that the implant component 54, when properly inserted in connector rod aperture 52, is held in the desired position along the spinal column. The surgeon can then secure the position of the implant component 54 and the connector 40 in relation to the attachment device 10 by tightening the link nut 60 on the tension link threaded end 32. This process is repeated, as necessary, along the spinal column at various points along the implant component 54. In this way, the surgeon has implemented the above described embodiments as a method for using the surgical implant system, for example, in repairing a degenerative spinal condition.

It is understood that the present invention has application outside the surgical implantation field. The polyaxial securing mechanism of the present invention is not limited to medical implants. The present invention, for example, could be used to secure guy wires or rods. In this application, the anchor screw could be inserted into the ground, e.g., set directly in to the soil, mounted in a concrete footing, or similar mounting. The guy wire or rod (i.e., the tension link) could then be inserted through the anchor screw and connected to the structure to be secured. The guy rod may include a turnbuckle. The turn buckle can then be adjusted to the desired tension in the guy rod. In this way, some room for error in the location of the anchor bolt is built into the installation process. The guy rod may be installed between the anchor screw and the structure without placing undue stress on the guy rod, or requiring unnecessary bending of the guy rod, due to misalignment between the connection point on the structure and the anchor bolt position. This is especially beneficial when a turnbuckle is implemented in the guy rod. The polyaxial nature of the anchor screw would allow the turnbuckle to be more easily adjusted since the stress within the guy rod is limited to the axial direction of the rod, i.e., no bending stress on the turnbuckle.

This is just one example of the possible applications of the present invention outside the field of medical implants. Other applications, by no means exhaustive, may include connecting legs of a tripod to a base and mounting track lighting fixtures.

Figure 20:
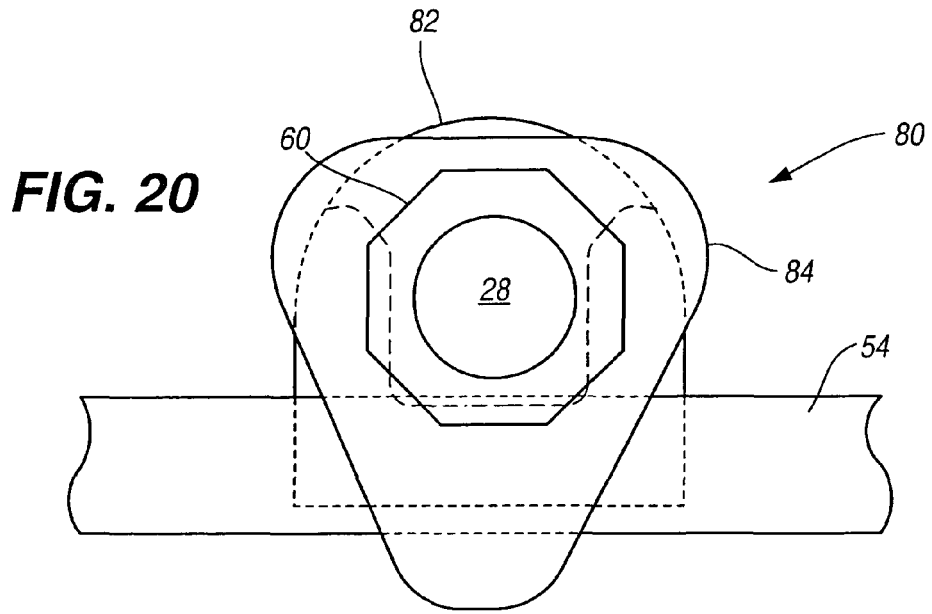
FIG. 20 is a top plan view of a separate embodiment of a connector.
Figure 21:
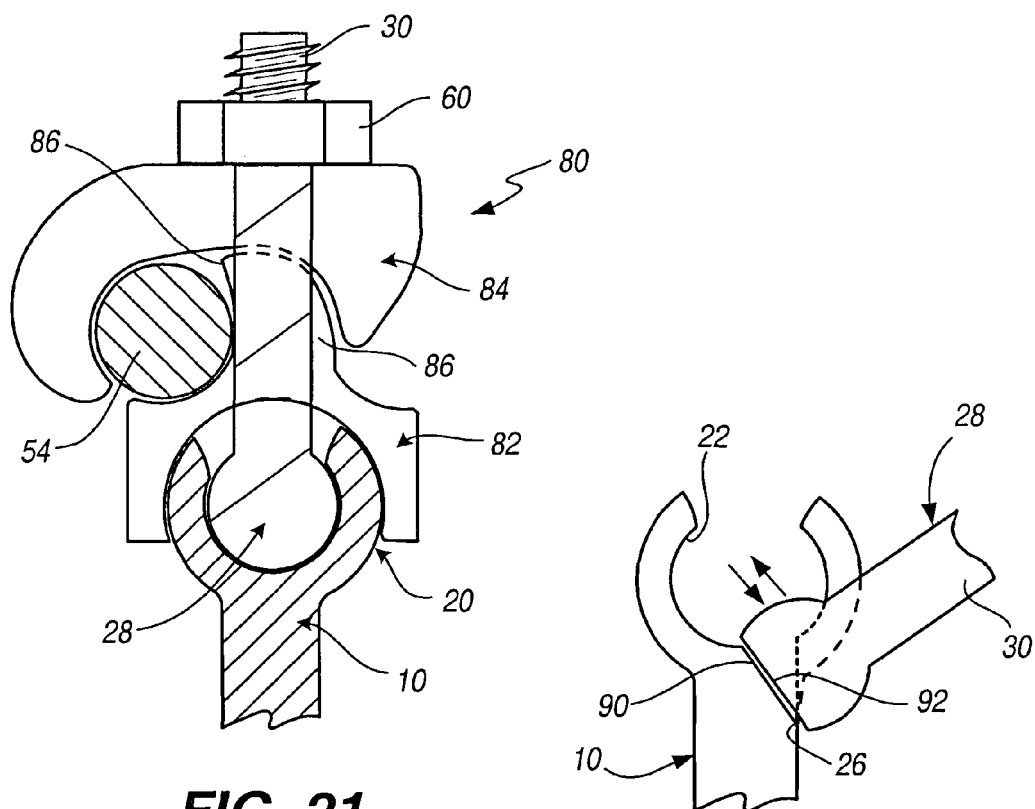
FIG. 21 is a side cross-sectional view of the connector shown in FIG. 20.

Referring now to FIGS. 20 and 21, a further aspect of the present invention is to provide a multi-piece connector 80. The advantage of a multi-piece connector 80 is its ability to offer different configurations for attachment of a rod 54 to bone screws or attachment devices 10 when geometry requirements of the implant area so dictate.

FIG. 20 is a top view of one possible configuration of an assembled multi-piece connector 80. FIG. 21 illustrates a side cross-sectional view of the same multi-piece connector 80. The multi-piece connector 80 includes a first anchor section 82 and a second hook section 84. The first anchor section 82 is positioned proximate the bone screw or attachment device 10. The second hook section 84 is positioned proximate the implant component or rod 54, such that it "hooks" around rod 54 and secures it against a cam 86 that is an integral part of first anchor section 82. After assembly of the multi-piece connector 80, a tension link 28 is used to secure the various components of the system together by tightening a tension link nut 60 at the distal end of the tension link 28. As may be appreciated, the aforementioned and described multi-piece connector or 80 is illustrated as having two pieces, however, multi-piece connectors 80 with more than two pieces is possible and appropriate for a potential application or patient's needs.

Figure 22:
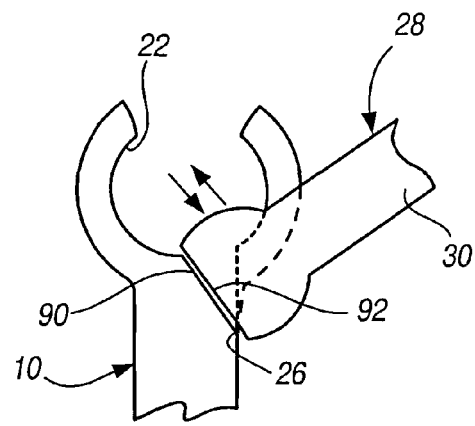
FIG. 22 is a side cross-sectional view of a separate embodiment of an attachment device and tension link having truncated portions.

Referring now to FIG. 22, in yet a further aspect of the invention, for attachment devices 10 having an entry channel 26 and an tension link slot 36, a truncated area 90 is incorporated into the entry channel 26 of the attachment device 10. In a corresponding manner, the head end 34 of tension link 28 possesses a corresponding flat or truncated area 92 that may be aligned with the truncated area 90. The attachment device 10 and tension link 28 are thereby mated for implanting such that they are configured in a manner that requires specific manipulation to enter and release the tension link 28 from the attachment device 10. These mating features allow the tension link 28 to be installed at the same time that the attachment device 10 is secured to the vertebra, with minimal chance that the tension link 28 will become uncoupled from the attachment device 10 prior to tightening using a tension nut because the tension link 28 has to be tipped to properly align the truncated areas 90 and 92 to release. However, this configuration allows the surgeon to remove the tension link 28 from the attachment device 10, if the surgeon so desires at some point during implantation. In this case, the surgeon would manipulate the tension link 28 to a proper angles such that it releases from the attachment device 10.

Figure 24:
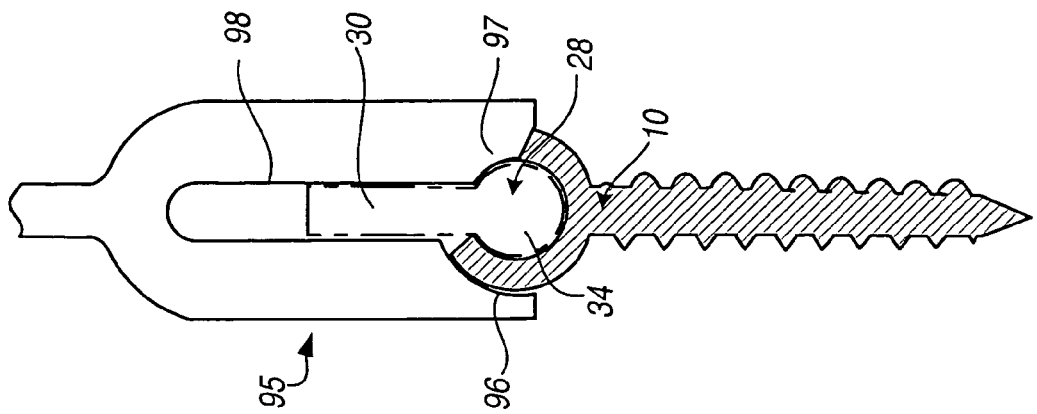
FIG. 24 is a cross-sectional view the receptacle end of the tool shown in FIG. 23.
Figure 23:
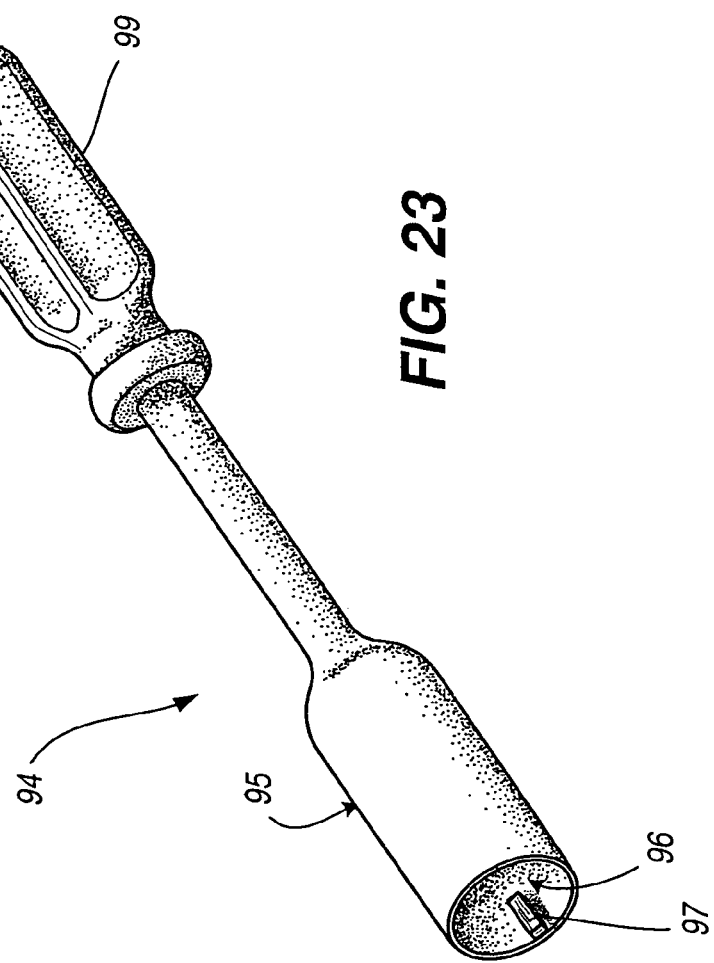
FIG. 23 is a perspective view separate embodiment comprising a tool to install the attachment device of the present invention.
Figure 25:
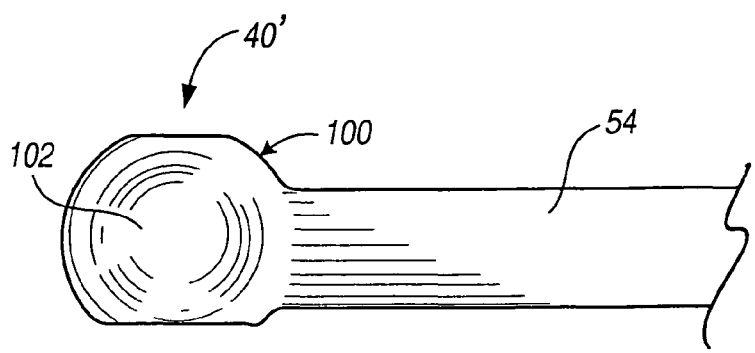
FIG. 25 is a side elevation view of a separate embodiment of an end connector.

Referring now to FIGS. 23 and 24, in a further embodiment of the invention, a tool 94 is provided to install the attachment device 10. The tool 94 possesses morphological or structural features that correspond to the shape of the attachment device 10 in such a way that the tool is used to provide both a downward force and a rotational force or torque to the attachment device 10, and thereby provide a means of implanting the attachment device 10 into the patient's bone. Therefore, the tool 94 possesses a tool receptacle end 95 that mates with the features of the enlarged area 20 of the attachment device 10. Specifically, the tool 94 preferably possesses a tool receptacle 96 that surrounds the outer and upper portion of enlarged area 20 of attachment device 10. More preferably, the tool 94 possesses a structure that mates with the hollow core 22 of the attachment device. More preferably yet, the tool 94 possesses a projection 97 that at least partially fits within the entry channel 26 of attachment device 10, and thereby allows the surgeon or installer to provide torque to the attachment device 10 by turning the tool, thereby providing force to screw the attachment device 10 into bone. Alternately, as shown in FIG. 24, the tool possesses a projection that at least partially fits into the tension link slot 36 of attachment device 10, and thereby allows the surgeon or installer to provide torque to the attachment device 10 to screw the attachment device 10 into bone. The tool 94 may also include a handle 99 or some other means that allows the tool 94 to be rotated by the surgeon. In summary, the tool 94 possesses a tool receptacle 96 that includes one or multiple projections 97 that at least partially fit into either the hollow core 22, the tension link slot 36, the entry channel 26, the expansion slot(s) 38, or any combination thereof, to allow the surgeon a means of providing torque to screw the attachment device 10 into bone.

Still referring to FIG. 24, in a different aspect of the tool embodiment, the tool 94 is used to install both the attachment device 10 and the tension link 28 at the same time. In use, the tension link 28 is fitted into the attachment device 10. Subsequently, the attachment device 10 and tension link 28 are simultaneously installed. Accordingly, the tool 94 preferably possesses a hollow interior shaft 98 that receivingly accepts the tension link shaft 30 of tension link 28. The tool receptacle 96 preferably fits over the upper and outer surface area of the enlarged area 20 of attachment device 10, with tension 28 in place. The receptacle 96 optionally includes a nylon, teflon or other type of insert to temporarily restrain the screw while the surgeon locates the location for insertion.

The tool 94 either possesses a projection 97 to at least partially fit into a structure of the attachment device 10, such as a tension link slot 36, or alternately, the tool 94 interacts with the enlarged area 20 of attachment device 10 utilizing a lathe-chuck-type of frictional fitting (not shown). The lathe-chuck-type of frictional fitting grasps the enlarged head area 20 of attachment device 10 and allows the surgeon means to provide torque to the attachment device 10 to screw the attachment device 10 into bone. Alternately, the enlarged head area 20 of attachment device 10 possesses facets (not shown) that allow a mating tool receptacle 96 to be placed over or around the enlarged head area 20 to thereby permit torque to be applied to the attachment device 10. In yet an alternate embodiment, a nut-like multi-faceted structure (not shown) that is an integral part of attachment device 10, and existing preferably below the enlarged area 20 and preferably at the upper regions of shank 12 is used to provide a means of grasping attachment device 10 with a tool capable of providing a torque force to attachment device 10 to screw attachment device 10 into bone.

Referring now to FIGS. 25-30, in a further embodiment of the present invention, an end connector 40' is incorporated directly into the rod 54 in the form of a receptacle 100. When placed at the end of a rod 54, the principal advantage of the end connector 40' feature is to shrink the profile of the attachment device 10, connector 40', and rod 54 configuration as a system, and thereby reduce the length of rod 54 that is longitudinally exposed beyond the attachment device 10 or screw location. In so doing, in spinal implant applications the next vertebra beyond the end of the rod is not exposed to potentially impacting the rod section that would have previously extended longitudinally beyond the connector location. This can reduce patient pain and increase patient mobility. A further advantage is that the smaller profile results in less tissue displacement in the vicinity of end connector 40'.

Figure 26:
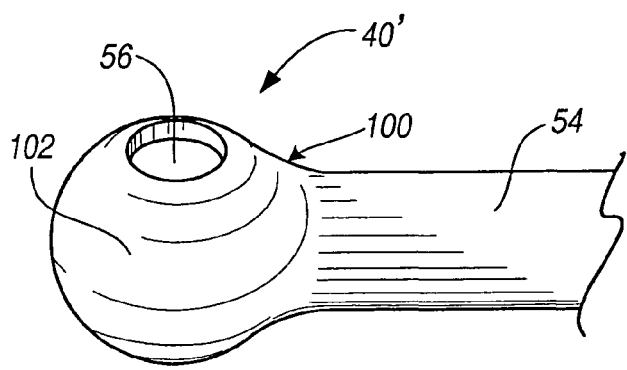
FIG. 26 is a perspective view of the connector shown in FIG. 25.
Figure 27:
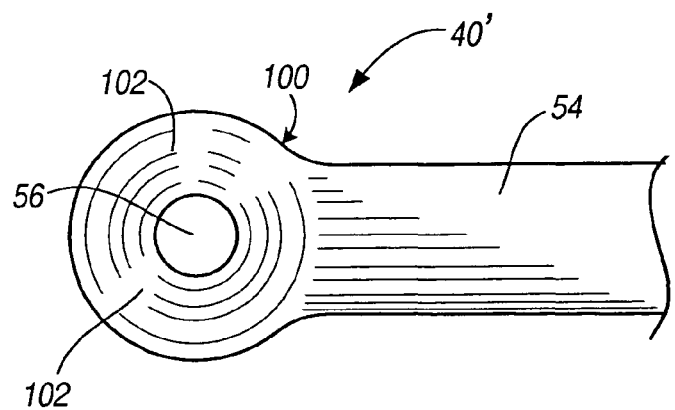
FIG. 27 is a top elevation view of the connector shown in FIG. 25.
Figure 28:
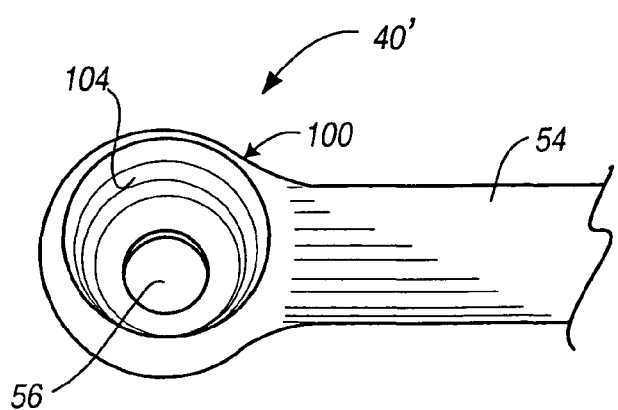
FIG. 28 is a bottom interior perspective view of the connector shown in FIG. 25.

Still referring to FIGS. 25-30, end connector 40' is shown located at the end of a rod 54; however, it is to be understood that the end connector 40' could be located within any portion of an implant. In a preferred embodiment, the end connector 40' includes a receptacle 100 that is in the form of a socket that preferably includes a socket exterior 102 and a socket interior 104. The socket interior 104 essentially acts as a low-profile connector. The socket interior 104 may be any shape that is configured to correspondingly accept an attachment device 10. Thus, the receptacle 100 is sized to fit over and receivingly accept the enlarged area 20 of the attachment device 10. Accordingly, socket interior 104 is preferably a recessed area at the end of a rod 54 that fits over the enlarged area 20 of the attachment device 10. As shown in FIG. 29, the socket interior 104 is preferably nearly semi-spherical, to match a spherical-type shape of enlarged area 20 of attachment device 10. However, socket interior 104 may be a vast variety of shapes that match the enlarged area 20 of the attachment device 10. Such shapes include rectangular cube, cubic, pyramid, ellipsoid, multi-faceted, conical, cylindrical, tetrahedral, elongated, combinations of these shapes, truncated portions of these shapes, or any other shape that may receivingly accept the enlarged area 20 of an attachment device 10. Within the center of the receptacle 100 is a tension link cavity 56 that is sized to accept the shaft 30 of the tension link 28. Referring to FIGS. 26-28, tension link cavity 56 can be seen as an opening through the top of receptacle 100.

FIGS. 29 and 30 show different views of attachment device 10, tension link 28, tension link nut 60, and receptacle 100. Installation of a rod 54 possessing the receptacle 100 would include installation of the attachment device 10, preferably by interconnecting the securement mechanism 18 of attachment device 10 to a target location on one of the patient's spinal vertebra or other bone segment. Subsequently, the tension link 28 is installed by feeding the shaft 30 of tension link 28 through the entry channel 26 of the attachment device 10, such that the shaft 30 of the tension link 28 is pulled through the central aperture 24 of the attachment device 10, thereby positioning the head end 34 of the tension link 28 within the hollow core 22 of the attachment device 10. Alternately, tension link 28 may be fitted into attachment device 10 prior to installation of the attachment device 10, or an attachment device having an expansion slot 38 may be used, whereby an entry channel 26 is not used to place the tension link head 34 into the hollow core 22 of the attachment device. In yet another alternative, the tension link 28 may be permanently mounted into attachment device 10 during manufacture, such that both the attachment device 10 and the tension link 28 form one piece of hardware, with the head end 34 of tension link 28 permanently mounted, but still rotatable, within the hollow core 22 of attachment device 10.

Following installation of the attachment device 10 with the tension link 28 in place, receptacle 100 of rod 54 is then placed over the attachment device 10 by feeding the tension link 28 through the tension link cavity 56 within the receptacle 100. The rod 54 is then secured to the attachment device 10 by advancing a tension link nut 60 on to the tension link 28.

The outside diameter of the receptacle 100 may vary depending upon the application; however, a diameter of about 10 mm is typical for receptacles 100 used in spine related surgery. The receptacle wall 105, defined as the area between the socket exterior 102 and socket interior 104, will preferably have a thickness necessary to provide sufficient structural confinement of attachment device 10 after tension link 28 is installed and link nut 60 is tightened on to shaft 30 of tension link 28. The thickness of the receptacle wall 105 will, therefore, depend upon the types of material used to make the various components, such as the receptacle 100, attachment device 10 and tension link 28.

In a separate embodiment, a receptacle 100 is positioned at each end (not shown) of a rod 54. In this manner, the rod 54 is used to span the distance between at least two attachment devices 10. Therefore, a series of various lengths of rods may be produced that permit the surgeon or installer to choose the correct length for any given installation. Alternately, a custom made rod may be produced to match the needs of the given installation requirements. Preferably, a rod 54 that is used to span a single vertebral joint is between 10 to 60 mm in length. However, lengths are determined on a case-by-case basis depending upon the patient's needs or the alternate application. For example, should the invention described herein be used in veterinary medicine, obviously the dimensions of the components will vary depending upon the size and type of animal undergoing treatment.

In a separate embodiment of the invention, one or more receptacles are located within the interior length of a rod. When receptacles are used at an interior rod location (not shown), the advantage to the patient is less tissue displacement. Here, individual receptacle locations may be produced within a length of rod, thereby reducing the need for use of a separate connector at each location along the length of the rod.

In still a separate embodiment, a continuous channel socket (not shown) is produced along the length of the underside of a rod. In this embodiment, individual tension link cavities may be drilled at the desired location just prior to implanting the rod. Alternately, the rod of this embodiment may be manufactured with a continuous tension link cavity (not shown) that possesses means for maintaining the position of a tension link and thereby prevents movement of the tension link along the longitudinal length of the rod. These means preferably include a series of shapes that maintain the position of the shaft of the tension link after the shaft it is fed through an individual tension link cavity of the continuous tension link cavity. The exterior surface of the enlarged area of attachment device may include detents or depressions that receivingly accept spring loaded balls or surficial features such as ridge texturing that is interconnected to the underside of continuous channel socket. Alternately, the surface features are preferably located on the exterior surface of the enlarged area of the attachment device, thereby interlocking with indentations located on the underside of continuous channel socket. Surficial features may include texturing, ridges, bumps, projections, protrusions, indentations, adhesives, and coverings or coatings of alternate materials.

A further inventive aspect comprises a clamp device. Among its many potential uses, the clamp feature is used to attach a new section of rod to an existing section of rod, to extend a section of rod, to provide length adjustability to a rod, to provide a means of attaching a separate structure to the end of a new or existing rod, to provide a means of attaching a separate structure to the end of a new or existing rod while adjusting the length of the rod, or to reinforce an existing section of rod. In general, the purpose of clamp is to allow the length of the rod to be adjusted at the surgical site without having to cut the rod, or custom order a length of rod, or use a standardized rod length that may not fit the patient.

Referring now to FIG. 31, a perspective view of one embodiment of the stabilizing assembly of the present invention is shown. The assembly includes a section of rod, or rod member, that is grasped by adjustable clamp 200. The clamp 200 is preferably comprised of two pieces that work to clamp the rod member, thereby forming a rod assembly that may be adjusted at the surgical site to accommodate different length requirements.

Figure 32:
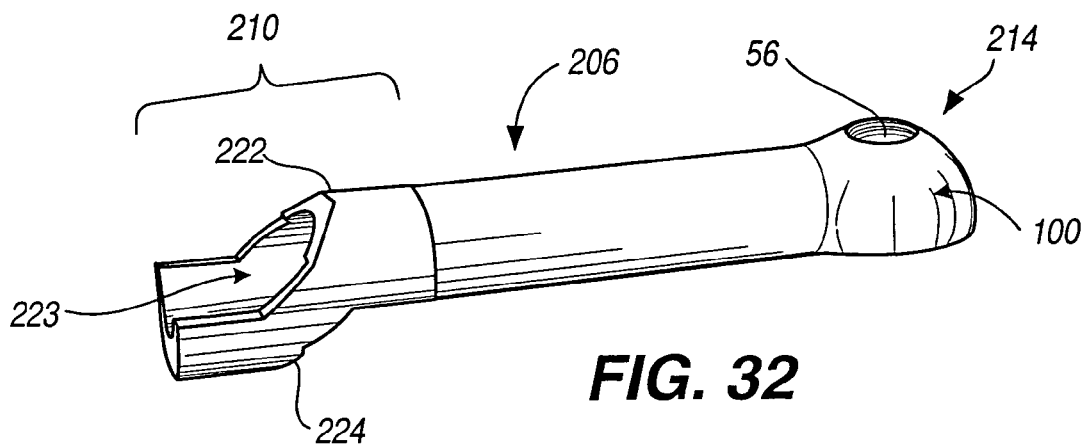
FIG. 32 is a perspective view of an upper clamp portion of the clamp.
Figure 33:
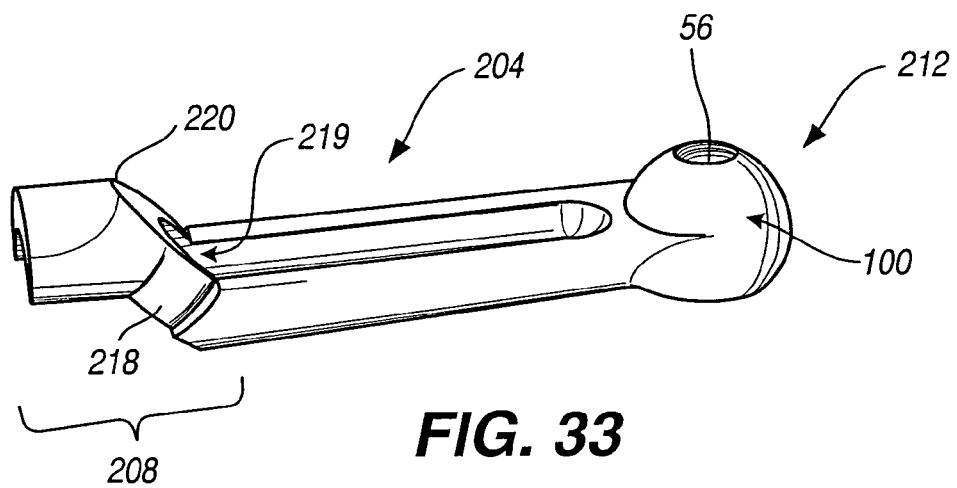
FIG. 33 is a perspective view of a lower clamp portion of the clamp.
Figure 34:
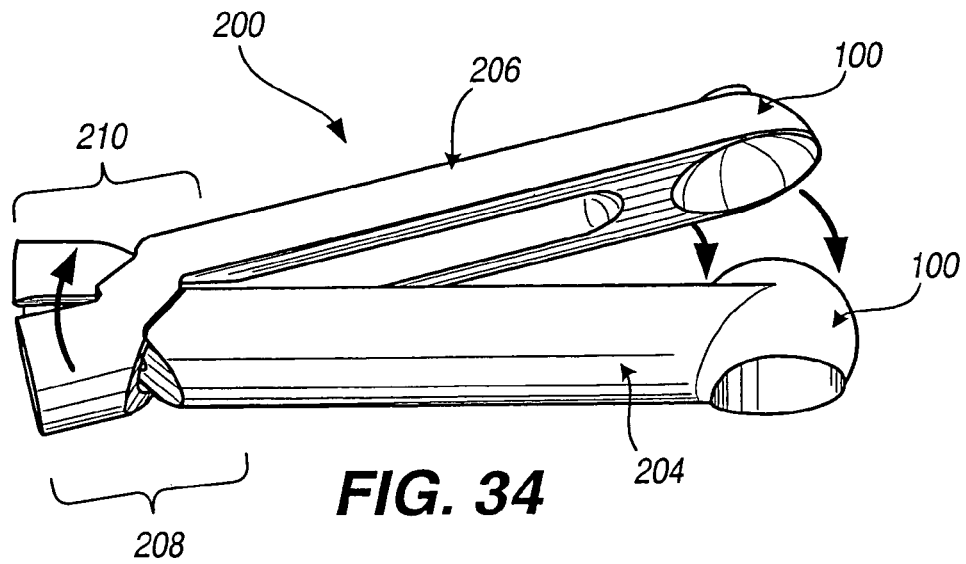
FIG. 34 is a perspective view of the lower and upper portions of the clamp in near interlocking proximity.

Referring now to FIGS. 31-34 the first piece in the assembly is the interior rod section or first rod member 202; the second piece is the lower clamp portion 204; and the third piece is the upper clamp portion 206. As shown in FIG. 33, lower clamp portion 204 includes a clamp region 208. Similarly, as shown in FIG. 32, upper clamp portion 206 includes a clamp region 210. The clamp regions 208 and 210 serve as an interlocking zone or compression zone. The lower clamp portion 204 and the upper clamp portion 206 interlock as shown in FIG. 34. During the interlocking of lower clamp portion 204 with upper clamp portion 206, the two pieces are brought together as shown in FIG. 34. The bringing together of the lower clamp portion 204 and the upper clamp portion 206 forces the two clamp regions 208 and 210 together. As shown in FIG. 31, upon complete assembly, such as after a surgical procedure, clamp regions 208 and 210 preferably substantially encircle or telescope around a portion of interior rod member 202. Accordingly, upon complete assembly, a portion of interior rod member 202 is preferably situated to the interior of lower clamp portion 204 and upper clamp portion 206 and is held in an interlocked configuration by the compressive forces acting in the clamp regions 208 and 210 of the lower and upper clamp portions 204 and 206.

Figure 35:
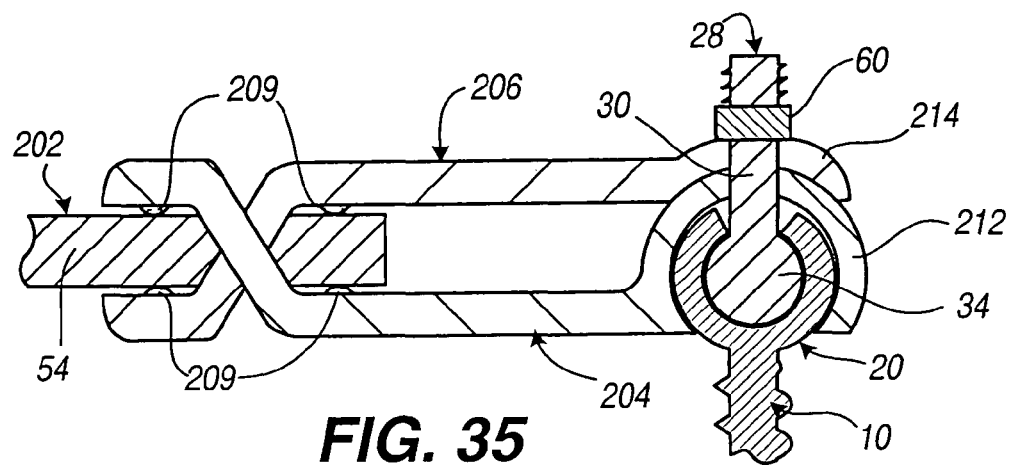
FIG. 35 is a cross-sectional view of a clamp having contact ridges.

Interior rod member 202 and clamp regions 208 and 210 may possess surface features that interlock and aid in securing the interior rod member 202 to the clamp regions 208 and 210. For example, clamp regions 208 and 210 may include detents or depressions that receivingly accept spring loaded balls or surficial features such as ridge texturing that is interconnected to the exterior surface of interior rod member 202. Surficial features may include texturing, ridges, bumps, projections, protrusions, indentations, adhesives, and coverings or coatings of alternate materials. For example, FIG. 35 illustrates a series of four ridges 209 that are used to concentrate pressure from the lower clamp portion 204 and upper clamp portion 206 to the interior rod member 202. Furthermore, although not required, openings through the lower clamp portion 204 and the upper clamp portion 206 may be used to receive securing devices such as pins, screws, bolts, hooks or anchors that interconnect the interior rod member 202 with the lower clamp portion 204 and/or the upper clamp portion 206. For example, although not required, at least one set screw may be used to interlock the interior rod member to one of the lower or upper clamp portions 204, 206. FIG. 31 illustrates the use of an optional set screw 211 to further interlock the interior rod member 202 with the upper clamp portion 206. The screw(s) can be oriented in a variety of directions to achieve this goal. Metal or resilient bands (not shown) may also be used to wrap and secure the interior rod member 202 with the lower clamp portion 204 and/or the upper clamp portion 206.

As shown in FIGS. 32-34, the lower clamp portion 204 includes a securing end 212, and upper clamp portion 206 includes a securing end 214. Securing ends 212 and 214 are used to secure the lower clamp portion 204 and the upper clamp portion 206 to the attachment device 10, such as by using a tension link 28. Accordingly, securing ends 212 and 214 are preferably sized to receive the enlarged area 20 of the attachment device 10. More particularly, the securing ends 212 and 214 preferably include receptacles 100 that receive the enlarged area 20 of the attachment devices 10. Preferably, the securing ends 212 and 214 include a socket-like shaped portion that fits over the enlarged area 20 of the attachment device 10. More preferably, securing end 212 fittingly cooperates with securing end 214. Although not required, securing end 212 and securing end 214, may also include surficial features (not shown) such as texturing, ridges, bumps, projections, protrusions, or indentations that cooperate with one another to prevent rotation or movement of the securing ends relative to one another once assembled.

Preferably, a tension link cavity 56 passes through securing ends 212 and 214, and provides for insertion of the shaft 30 portion of tension link 28 through securing ends 212 and 214. Link nut 60 may be used to secure the lower clamp portion 204 and the upper clamp portion 206 to the tension link 28, and therefore to the attachment device 10. Furthermore, by tightening the link nut 60 that is threaded onto the tension link 28, the lower clamp portion 204 and the upper clamp portion 206 are brought together in tight cooperation. This action tightens clamp region 208 and clamp region 210 around interior rod member 202, thereby securing interior rod member 202 from movement longitudinally relative to lower clamp portion 204 and upper clamp portion 206. Accordingly, clamp 200 shares similarities to a pliers-type tool by utilizing a compression force at the securing ends 212 and 214 of the lower clamp portion 204 and the upper clamp portion 206 to create a compression force around the interior rod member 202 at the clamp regions 208 and 210. The interlocking feature of the clamp 200 shares similarities to a pair of pliers because the compression force exerted at one end, the securing ends 212 and 214, is translated to compression forces at the interlocking zone, or compression zone, or clamp regions 208, 210. In addition, the installation of the clamp 200 shares similarities to forceps used in obstetrics during the delivery of a baby, whereby the device is assembled in pieces to provide a means of grasping the intended object. In the case of the present invention, however, means are employed to secure the grasping function or clamp regions 208 and 210 of the clamp 200 by tightening the securing ends 212 and 214 of the lower clamp portion 204 and upper clamp portion 206.

Lower clamp portion 204 and the upper clamp portion 206 are preferably of a shape that is approximately a half-cylinder. More preferably, as shown in FIGS. 32-34, the half-cylinder shapes include bends in the clamp regions 208 and 210. In this aspect, the lower clamp portion 204 bends within clamp region 208 to encompass the upper region of interior rod member 202 after the assembly is complete. Similarly, the upper clamp portion 206 bends within clamp region 210 to encompass the lower region of interior rod member 202 after the assembly is complete. More specifically, in a preferred embodiment, the lower clamp portion 204 includes a first bend 218 at the lower side of interior rod member 202, and a second bend 220 at the upper side of interior rod member 202. In a similar but mirrored fashion, upper clamp portion 206 includes a first bend 222 at the upper side of interior rod member 202, and a second bend 224 at the lower side of interior rod member 202.

Between the first bend 218 and the second bend 220 of the lower clamp portion 204, the lower clamp portion 204 includes an opening 219 wherein interior rod member 202 is slidably received when the interior rod member 202, lower clamp portion 204, and upper clamp portion 206 are assembled. Similarly, between the first bend 222 and the second bend 224 of the upper clamp portion 206, the upper clamp portion 206 includes an opening 223 wherein interior rod member 202 is slidably received when the interior rod member 202, lower clamp portion 204, and upper clamp portion 206 are assembled.

Among a number of favorable characteristics, the clamp 200 essentially allows the length of the structural member (typically a rod) spanning two bone screws or attachment devices 10 to be adjusted at the surgical site without having to cut the rod because the length of the rod is adjustable by moving the interior rod member 202 within the lower clamp portion 204 and the upper clamp portion 206 prior to fixing securing ends 212 and 214 by securing an interconnecting mechanism, such as by tightening a link nut 60. This eliminates the need for having to custom order a length of rod, or otherwise use a standardized rod length that may not fit the patient, and thereby cause decreased performance and potentially increased pain to the patient. Furthermore, utilizing the components of the present invention, the entire assembly can be tightened by securing a link nut 60 at each attachment device 10 after the interior rod member 202 is placed within the lower clamp portion 204 and the upper clamp portion 206. This greatly simplifies the surgeon's efforts and serves to reduce operation time and associated patient risk.

Figure 36:
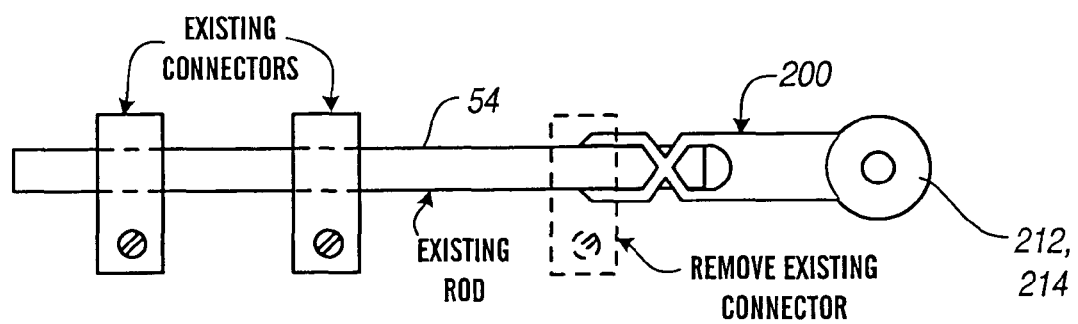
FIG. 36 is a plan view of a separate embodiment of the clamp, wherein the clamp is being retrofitted to an existing rod segment.

In addition to the above noted characteristics inherent to using a rod implant with the clamp 200 feature, the clamp 200 is also especially applicable to adding an additional length of rod 54, or providing length adjustability to a rod being implanted concurrently with the implantation of the clamp 200 device, or can be used to add additional length to an already existing portion of rod that had previously been implanted into the patient during a prior surgical procedure. A method for subsequently retro-fitting a portion of rod possessing the clamp 200 to an existing portion of rod is now presented.

Where an existing rod implant exists, the patient's surgical site would be partially exposed at the end of the existing rod requiring extension. If a sufficient length of rod or rod run-out length exists beyond an existing rod connector that attaches the existing rod to the bone, then the clamp 200 may be interconnected directly to the rod run-out length with additional length of new rod implanted as the patient's conditions may warrant. Alternately, if sufficient rod run-out length does not exist, as shown in FIG. 36, then the first existing connector can be removed, thereby exposing a sufficient length of rod for the clamp 200 to clamp the existing rod. More than one connector may have to be removed in certain cases.

Figure 37:
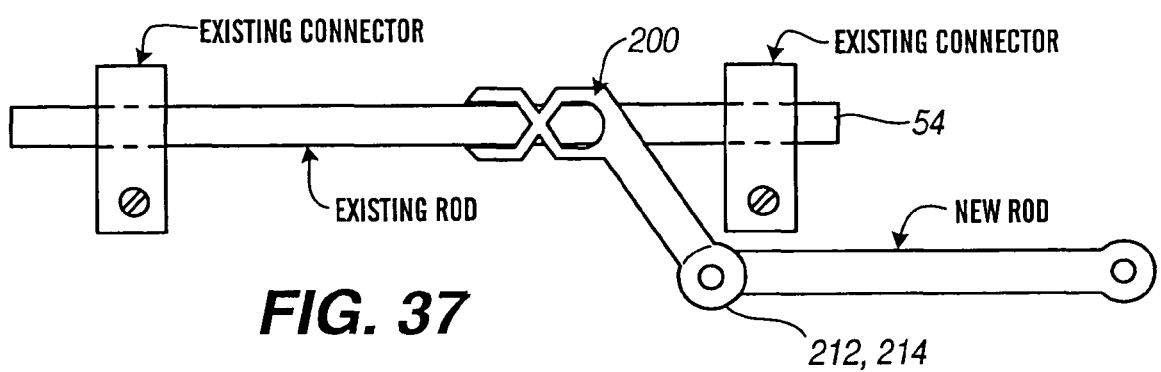
FIG. 37 is a plan view of yet a separate embodiment of the clamp, wherein the clamp is again being retrofitted to an existing rod segment.
Figure 40A:
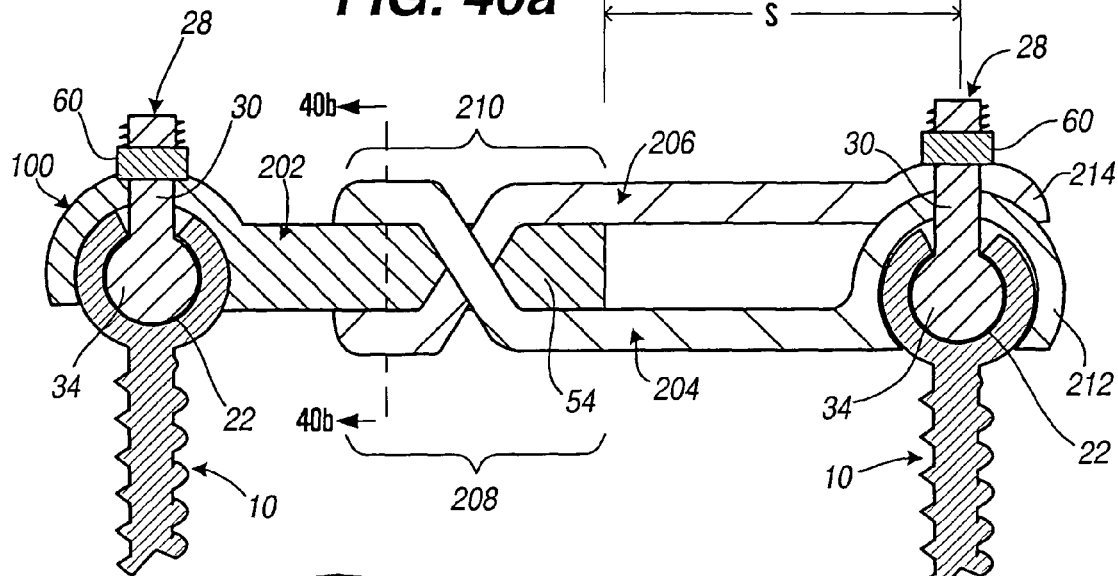
FIG. 40a is a side cross-sectional view of one of the stabilization assemblies shown in FIG. 38.
Figure 40B:
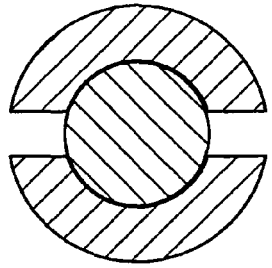

A further option comprises clamping the clamp 200 over a sufficient length of rod that may be accessible between existing connectors. Here, the clamp 200 would preferably include at least one additional bend as shown in FIG. 37. Alternately, two additional bends may be used in order to align the clamp portions of the clamp 200 between the existing connectors. This option then eliminates the necessity for removing at least the first existing connector. The advantage of the above listed methods for attaching the clamp 200 invention to an existing rod is that the existing rod does not have to be completely exposed and removed, with a new longer rod implanted. Therefore, a smaller incision is necessary and consequently, multiple benefits are realized including decreased medical costs and less pain to the patient. Another advantage is that a second parallel rod does not need to be installed adjacent the first existing rod. Accordingly, structural support can be achieved in the form of an extension using clamp 200 and adapting the lower clamp portion 204 and the upper clamp portion 206 to accept the existing rod.

Referring now to FIGS. 38-40a-b, in a separate embodiment, an assembly is provided that utilizes the various components listed above. Thus, one application of this embodiment then is the installation of two separate attachment devices 10 that are then fitted with the other devices. In use, attachment devices 10 are installed first. In one preferred method of use, the attachment devices 10 are pedicle screws that are installed into two vertebra, a first vertebra $V_1$ and a second vertebra $V_2$. More preferably, as shown in FIG. 38, right and left assemblies are installed on either side of the spinous process. Installation of the attachment devices 10 is followed by the installation of tension links 28 through or into the two attachment devices 10. Alternately, the tension links 28 may be placed into the attachment devices 10 prior to installing the attachment devices 10 into their intended positions. Subsequent to installing the attachment devices 10 with the tension links 28 in place, an interior rod member 202 having a receptacle 100 and a rod member 54 is implanted over one of the attachment devices 10 and secured with a first link nut 60. Installation of interior rod member 202 is preferably performed in conjunction with installing a lower clamp portion 204 and an upper clamp portion 206 over the remaining attachment device 10 while clamping the clamp regions 208 and 210 of the lower clamp portion 204 and an upper clamp portion 206, respectively, around the interior rod member 202. Subsequently, securing ends 212 and 214 are securely attached to the second attachment device 10 by placing a second link nut 60 onto the exposed portion of the tension link 28 of the second attachment device 10. Of course, the clamp regions 208 and 210 may be adjusted during tightening securing ends 212 and 214 using second link nut 60 to ensure an appropriately configured arrangement of interior rod member 202, clamp 200, attachment devices 10, and tension links 28. The resulting assembly spans disk D. Accordingly, the interior rod member 202 serves as a first rod member, and the lower clamp portion 204 and an upper clamp portion 206 serve as a second rod member that combine to structurally bridge disk D when interconnected to attachment devices 10 by interconnecting mechanisms, such as tension links 28.

Figure 41:
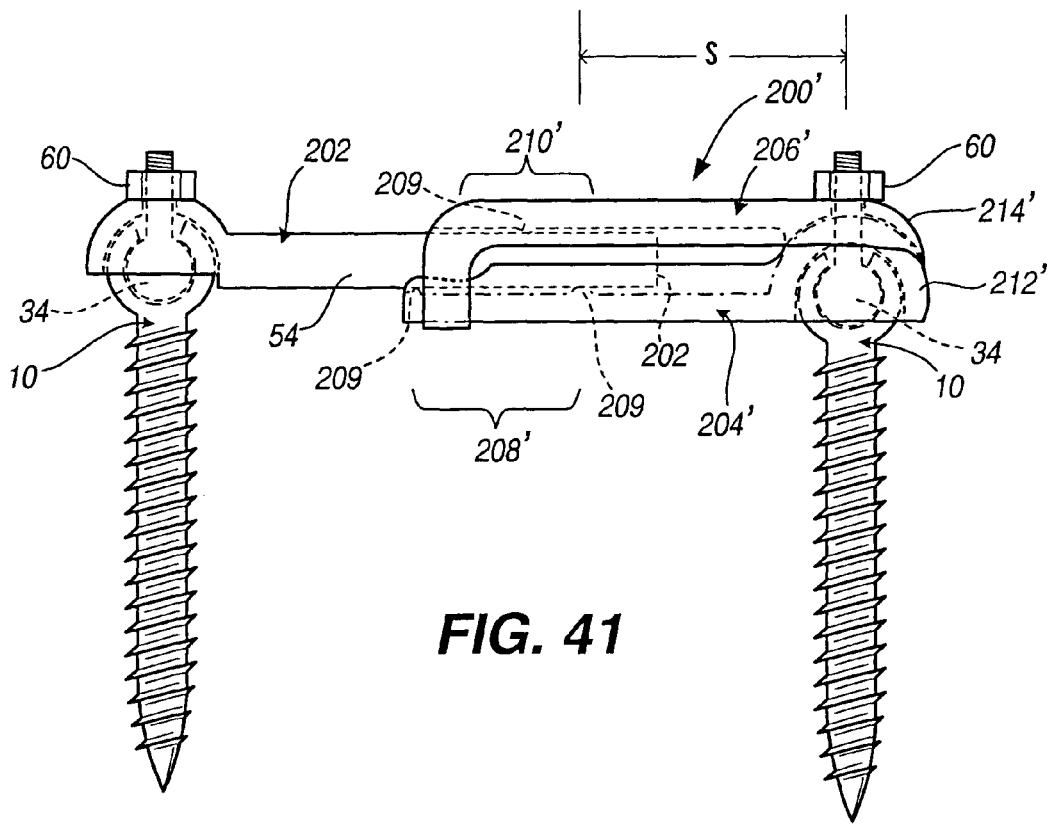
FIG. 41 is side elevation view of stabilization assembly having a separate embodiment of a the clamp device.

Referring now to FIG. 41, a separate embodiment of the clamp 200' is provided wherein the clamp 200' includes a lower clamp portion 204' and an upper clamp portion 206'. This embodiment provides a different configuration for the clamp. However, similar to the clamp 200 described above, the compressive forces are applied by the clamp regions 208' and 210' by tightening the securing ends 212' and 214' using an interconnection mechanism, which preferably is a link nut 60 applied to a tension link 28. As shown in FIG. 41, ridges 209 may be used within the interior of lower clamp portion 204' and an upper clamp portion 206'. As shown in FIG. 41, three ridges 209 are used, thereby wedging interior rod member 202 between the lower clamp portion 204' and an upper clamp portion 206' when link nut 60 is tightened. Thus, it is to be understood that the present invention encompasses various embodiments whereby an interlocking force can be applied to a clamp region of a structure that is at a spaced distance S away from the securing ends.

Figure 42A:
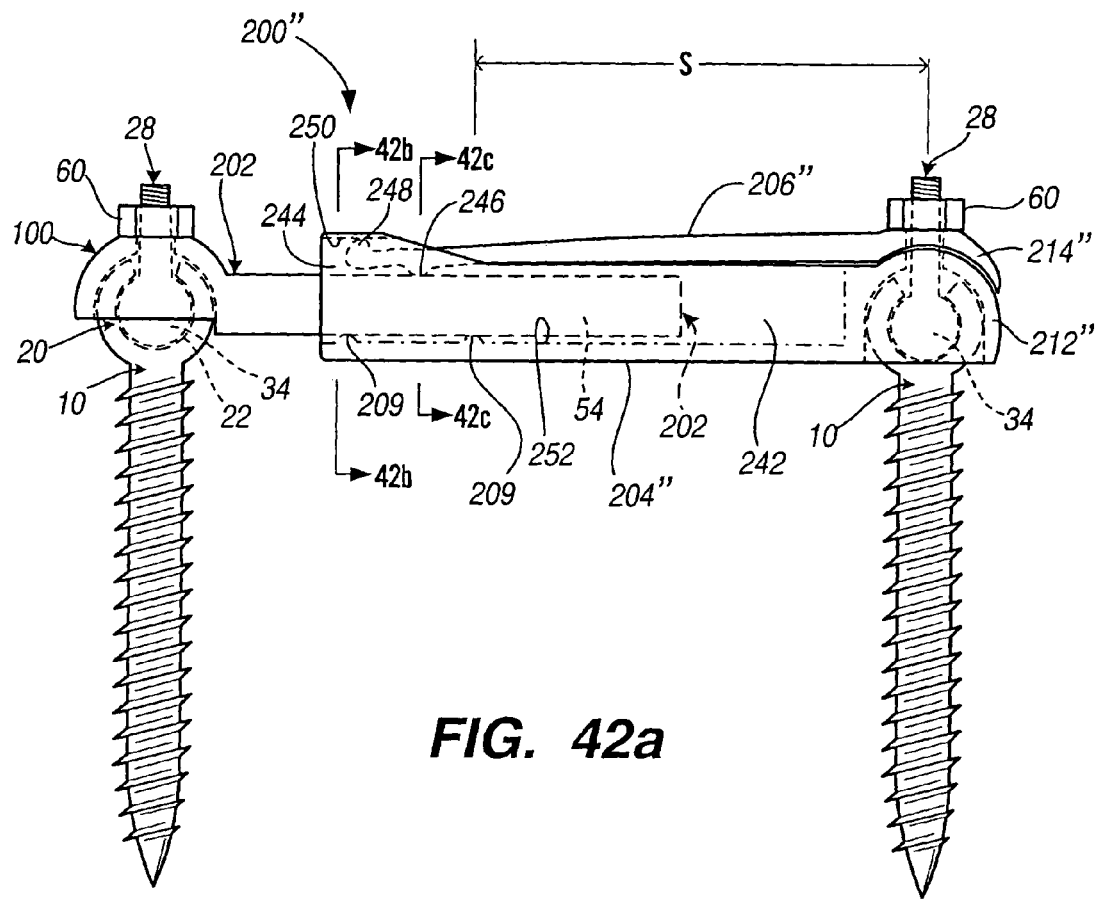
FIG. 42a is side elevation view of a stabilization assembly having yet a separate embodiment of a the clamp device.
Figure 42B:
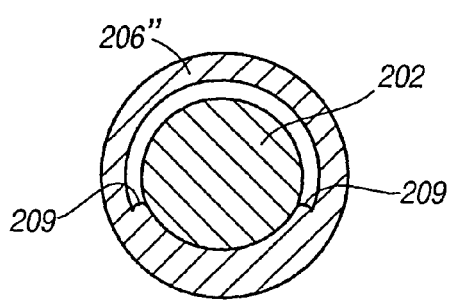
Figure 42C:
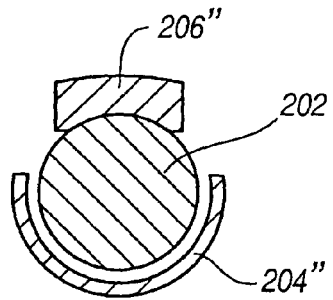

Referring now to FIG. 42a-c, a further illustrative example of an alternate embodiment of the clamp is shown. Clamp 200" includes a lower clamp portion 204" and an upper clamp portion 206". Lower clamp portion 204" includes a hollow interior 242 for receiving interior rod member 202. The hollow interior 242 also includes an upper space 244 for receiving upper clamp portion 206". Upper clamp portion 206" is a member that includes a heal projection 246 and a toe projection 248. Upon tightening the securing end 214" of upper clamp portion 206", the heal projection 246 presses down on interior rod member 202 while the toe projection 248 presses up on an upper interior surface 250 of lower clamp portion 204". Upper clamp portion 206" may be biased to increase the forces applied to its heal projection 246 and toe projection 248 when it is tightened into place. The resulting forces compress and interlock the interior rod member 202 against the lower interior surface 252 of lower clamp portion 204", thereby securedly holding interior rod member 202 within the lower clamp portion 204" and upper clamp portion 206". As shown in FIG. 42a, two ridges 209 are preferably provided along the lower interior surface 252 of lower clamp member 204". The two ridges 209 are spaced apart such that heal projection 246 of upper clamp portion 204" is positioned intermediate the two ridges, thereby providing a triangulated force pattern on interior rod member 202.

Referring now to FIG. 43, a separate embodiment comprising a telescoping rod 230 is shown. The telescoping rod 230 preferably has a receptacle 100 placed at each end of the telescoping rod 230. An inner first rod portion 232 slidably receives a second outer rod portion 234, thereby allowing adjustment of the length of the rod prior to securing the receptacles over previously installed attachment devices 10 with corresponding tension links 28. The telescoping rod may be configured such that one portion fits within another portion, as shown, or one portion of the rod may be positioned above or below the other portion. The telescoping portions may interlock without the use of additional components by, for example: means of a friction fit between the telescoping portions; locking collars; pins; etc. One aspect of a preferred embodiment bares similarities to a Chinese finger trap toy, whereby movement is allowed in one direction, but resisted in the other direction. Alternately, the sections of the telescoping rod may thread into one another, thereby providing both a length adjustment feature and a locking feature. Alternately yet, the telescoping portion of the rod may optionally be secured using securing means such as a bolt, set screws 211 (as shown in FIG. 43), band, or other similar device, or multiple such devices. In yet another alternative, a shim of various possible shapes including tapered regions may be pushed into or otherwise placed along a portion of the length of the telescoping rod segments in order to lock the segments together. In yet another alternative, the rod may be adjusted to its final intended length and secured using adhesives or an epoxy such as methyl metacrylate. The adhesives or epoxy may be applied to the surface of portions of the telescoping rod, or alternately, it may be injected in one or more injection ports. The telescoping rod may also feature a resilient member 236, such as a spring, within the rod to provide an expansive force between the two portions of rod.

Referring now to FIG. 44a, in a separate embodiment of the invention, the tension link 28 includes additional features that render it particularly suited to implanting during a surgical operation. It is known that a substantial number of implants involve the spanning or bridging of one vertebral disc. Therefore, one aspect of the present invention is to consecutively install the first and second attachment devices 10 with tension links 28 possessing extended shafts 30'. Specifically, the tension link 28 preferably is available in variable lengths. More preferably, the tension link 28 is long enough to provide easy manipulation while being implanted. More preferably yet, the tension link 28 has an extended shaft 30' that is substantially longer than is necessary, but is capable of being trimmed during the surgical implanting procedure. Here, the tension link 28 with an extended shaft 30' may preferably be 10 to 150 millimeters longer than necessary, and more preferably, 20 to 120 millimeters longer than necessary, and more preferably yet 40 to 80 millimeters longer than is necessary.

The extended shaft 30' is preferably used as a guide by the surgeon to provide a means of placing the interior rod member 202 having receptacle 100 and rod 54, clamp 200 including lower and upper clamp portions 204 and 206 having securing ends 212 and 214, and link nuts 60. Accordingly, each extended shaft serves to guide the stabilizing structures to be implanted. In use, the surgeon first installs the attachment device 10 either with or without the tension link 28 already in place. If the tension link 28 is not installed concurrently with the attachment device 10, the surgeon installs the tension link 28 after the attachment device 10 has been installed. After installation of the attachment device 10 and tension link 28, the extended shaft 30' is used to guide the interior rod member 202 possessing a receptacle 100 down to the enlarged area 20 of attachment device 10. As a further example, the other tension link 28 with an extended shaft 30' would serve to guide both clamp portions of clamp 200. That is, lower clamp portion 204 and upper clamp portion 206 with securing ends 212 and 214 are guided down to and placed over the end of the second attachment device 10. Thus, these components may be slid down to the enlarged areas 20 of attachment devices 10 in one effort. Subsequently, tension link nuts 60 are slid down the extended shafts 30' of tension links 28, and may be fully or at least partially threaded onto the threaded portions of shaft 30 of the tension links 28. Subsequent to using the extended shaft 30' as a guide to the head of the attachment device 10, the extended shaft 30' is trimmed using a shearing tool familiar to those in the art, or the extended shaft 30' is broke along a pre-existing score 238, as shown in FIG. 44b. Thus, the extended shafts 30' of the tension links 28 are preferably trimmed by a surgical staff member, leaving a sufficient threaded portion in place to hold link nut 60. The extended shaft 30' is then discarded, leaving the trimmed tension link shaft 30 in place with the link nut 60 attached thereto. This embodiment offers the advantage being a minimally invasive surgical procedure by providing means of performing spinal stabilization surgery, by supplying surgical implant devices and methods that significantly limit the length of the surgical incision and the length of time necessary to perform the surgery. Thus, benefits are realized in the form of smaller incisions, less tissue displacement, less patient pain and recovery time, shorter surgical time, less cost, and less fatigue of surgical staff.

A further aspect of the above noted embodiment is the use of a flexible extension or leader (not shown) on to the end of the shaft 30 of tension link 28. In this aspect of the invention, the substantially rigid portion of shaft 30 of tension link 28 is fitted with a relatively flexible leader extending along the axis of the longitudinal axis of shaft 30 of tension link 28. The flexible leader is preferably attached to the tension link 28 sometime prior to surgery, and more preferably sometime during manufacture of the tension link 28. The flexible leader then serves to provide means of guiding any additional components down to the attachment device 10 as may be desired. The flexible leader is preferably made of a material capable of being manipulated without breaking during surgery. More preferably, the flexible leader is made of a metallic wire material or a plastic material. More preferably yet, the flexible leader is easily separated from the end of shaft 30 of tension link 28 after any desired stabilizing components are installed. Accordingly, an extended tension link 28 may take the form of simply an extended shaft 30', or it may take the form of a regular sized tension link 28 shaft 30 with a flexible leader attached thereto.

Other than the flexible leaders discussed above, the interior rod member 202, lower clamp portion 204, upper clamp portion 206, rod 54, connectors 40, receptacles 100, attachment devices 10, tension links 28, and link nuts 60 and other structural features described herein are made from a material that possesses the appropriate strength characteristics necessary to withstand loading from the human body when used in medical applications. Tensile strength qualities of the materials used is a key consideration. Preferably, materials may include ceramics, plastics, metals, or carbon fiber composites. More preferably, the materials are made from titanium or stainless steel.

Devices disclosed herein can also be made of thermal memory materials or materials that possess different elastic properties at varying temperatures. In this aspect of the invention, the subject component(s) may be heated or cooled to a desired temperature, implanted, then subsequently allowed to cool or warm to the temperature of the ambient conditions that will exist during the usage period for the subject device, namely, normal body temperature.

The dimensions of the rod features may vary considerably depending upon the patient's needs. For example, a rod the entire length of the spine, such as 2 feet in length, may be used. Alternately, a rod only 10 mm long may be all that is necessary to span and bridge the target segment of the spine. Therefore, the preferable length of rod is simply an adequate length to bridge the necessary vertebral disc or discs.

The curvature of the rod may also be variable depending upon the desired final curvature sought for the patient. The curvature may be established during manufacture of a given rod, and/or a given rod segment may have its curvature adjusted at the of time surgery prior to implantation.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A surgical implant assembly for attachment to a bone, comprising:
    an integral attachment device having first and second ends, said first end adapted for securing to the bone, said second end having a hollow core bordered by curved walls, said second end having a central aperture contiguous with said hollow core, said second end further including at least a second opening wherein said second opening is at least one of an expansion slot and an entry channel;
    a tension link having a proximal end and a distal end, said proximal end having a tension link head and said distal end being threaded, said tension link head rotatably mounted within said hollow core and maintained therein by contact with said curved walls; and
    a rod having at least one integral preformed socket adapted for at least partially receiving said second end of the attachment device, said socket including at least one tension link cavity, wherein said rod is secured to said attachment device by a tension link nut that is threaded onto said distal end of said tension link.

2. The surgical implant assembly of claim 1, wherein said first end of said integral attachment device includes threads.

3. The surgical implant assembly of claim 1, wherein said integral preformed socket is at least partially spherical in shape.

4. The surgical implant assembly of claim 1, wherein said integral preformed socket is located at an end of said rod.

5. A method of installing a surgical implant assembly to a human bone, comprising the steps of:
    (a) securing an integral attachment device to the human bone, the integral attachment device having a shank with first and second ends, the first end adapted for securing to the human bone, the second end having a hollow core and a central aperture, said second end further including at least a second opening comprising an entry channel operatively connected with the hollow core;
    (b) inserting a tension link head of a tension link into the hollow core of the integral attachment device, the tension link having a tension link shaft that extends through the central aperture of the integral attachment device;
    (c) seating a rod having an integral socket-shaped connecting receptacle onto the second end of the integral attachment device by passing the tension link shaft through a tension link cavity within the integral socket-shaped connecting receptacle; and
    (d) securing the rod to the integral attachment device by threading and tightening a tension link nut onto the tension link shaft.

6. The method of claim 5, further comprising the step of adjusting an angular relationship between the integral attachment device and the integral socket-shaped connecting receptacle.

7. The method of claim 6, wherein said adjusting step occurs between steps (c) and (d).

8. The method of claim 5, wherein said inserting step further comprises inserting the tension link shaft through the entry channel and the hollow core, and pulling the tension link shaft through the central aperture until the tension link head is positioned in the hollow core.

9. A method of installing a surgical implant assembly to a human bone, comprising the steps of:
  (a) securing an integral attachment device to the human bone, the integral attachment device having a shank with first and second ends, the first end adapted for securing to the human bone, the second end having a hollow core and a central aperture, said second end further including at least a second opening comprising an entry channel having an entrance operatively connected with the hollow core, and a tension link slot through the second end to the hollow core between the entry channel and the central aperture;
  (b) inserting a tension link head of a tension link into the hollow core of the integral attachment device, the tension link having a tension link shaft that extends through the central aperture of the integral attachment device, said inserting step comprising placing the tension link head at the entrance of the entry channel, inserting the tension link shaft into the tension link slot such that the tension link shaft is located within the central aperture, and pulling the tension link head into the hollow core;
  (c) seating a rod having an integral socket-shaped connecting receptacle onto the second end of the integral attachment device by passing the tension link shaft through a tension link cavity within the integral socket-shaped connecting receptacle; and
  (d) securing the rod to the integral attachment device by threading and tightening a tension link nut onto the tension link shaft.

10. In subcombination, a low-profile medical device connector used to connect a piece of hardware to a spine, the connector device used in combination with a tension link having a tension link head and a tension link shaft that threadably receives a tension link nut, and in combination with an integral attachment device having a portion adapted for securing to the spine, a substantially spherical shaped area with a hollow core for receiving the tension link head, a central aperture for passing the tension link shaft therethrough, and at least a second opening wherein the second opening is at least one of an expansion slot and an entry channel, said connector device comprising:
  a rod portion including a rod member adapted for aligning substantially parallel to the spine when implanted and adapted for at least partially spanning at least one disk of the spine when implanted, said rod portion further including an integral receptacle attached to said rod member, said integral receptacle including a substantially semi-spherical shaped socket adapted to receive the substantially spherical shaped area of the integral attachment device, said integral receptacle having a tension link cavity for passing the tension link shaft therethrough;
  wherein said socket is rotatable over said substantially spherical shaped area of the integral attachment device before securing said rod portion to said integral attachment device, and wherein said rod portion is secured to the integral attachment device by tightening the tension link nut on the tension link shaft after passing the tension link shaft through said tension link cavity upon placement of said integral receptacle over the integral attachment device.

* * * * *